(12) United States Patent
Gautschi et al.

(10) Patent No.: US 6,939,845 B2
(45) Date of Patent: Sep. 6, 2005

(54) FRAGRANCE PRECURSORS

(75) Inventors: Markus Gautschi, Zeiningen (CH);
Caroline Plessis, Yvre le Polin (FR);
Samuel Derrer, Fällanden (CH)

(73) Assignee: Givaudan SA, Vernier (CH)

( * ) Notice: Subject to any disclaimer, the term of this patent is extended or adjusted under 35 U.S.C. 154(b) by 513 days.

(21) Appl. No.: 09/883,409

(22) Filed: Jun. 18, 2001

(65) Prior Publication Data

US 2002/0035055 A1 Mar. 21, 2002

(30) Foreign Application Priority Data

Jun. 19, 2000 (EP) .............................................. 00111981

(51) Int. Cl.⁷ .......................... A61K 7/46; C07C 49/115; C07C 49/215; C07C 49/782
(52) U.S. Cl. .............................. 512/25; 512/2; 568/303; 568/308; 568/325; 568/326; 568/327; 568/328; 568/329; 568/331; 568/337; 568/376; 568/377; 568/579; 568/626; 568/659; 568/660; 568/664; 568/665; 568/670
(58) Field of Search ....................... 512/2, 25; 568/303, 568/308, 325, 326, 329, 331, 376, 377, 579, 626, 659, 660, 664, 665, 670, 327, 328, 337

(56) References Cited

U.S. PATENT DOCUMENTS 5,162,588 A * 11/1992 Fehr et al. .................. 568/328
6,492,563 B2 * 12/2002 Gautschi et al. ............ 568/327

FOREIGN PATENT DOCUMENTS

EP 0 936 211 A2 8/1999
WO WO 99/60990 12/1999

OTHER PUBLICATIONS

Greene, T.W., *Protective Groups in Organic Synthesis*, 2nd Edition, 31–34 (1991).
Dixon, D.D., et al., *Synlett*, 1093–1095 (1998).
Brunckova, J., et al., *Tetrahedron*, 51, 11945–52 (1995).
Cowper, R.M., et al., *Org. Synth. Coll.*, 2:480–81 (1943).
Noe, V.C.R., et al., *Angew. Chem.*, 100: 1431–1433 (1988).
B.T. Cho et al.: Tetrahedron: Asymmetry 10 (1999) 1843–1846, "A practical method for synthesis of terminal 1,2–diols in high enantiomeric excess via oxazaborolidine–catalyzed asymmetric reduction".

* cited by examiner

*Primary Examiner*—Monique T. Cole
(74) *Attorney, Agent, or Firm*—Norris McLaughlin & Marcus PA

(57) ABSTRACT

The present invention provides a fragrance precursor of formula I:

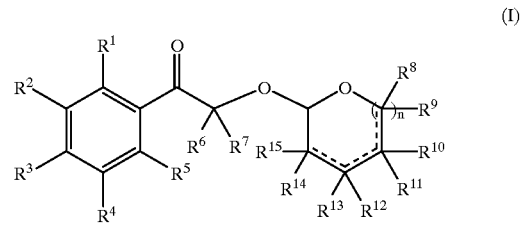

(I)

that is capable of forming a fragrant ketone of formula II:

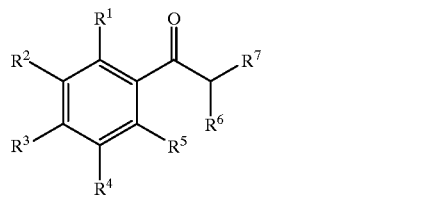

(II)

and a fragrant lactone of formula III:

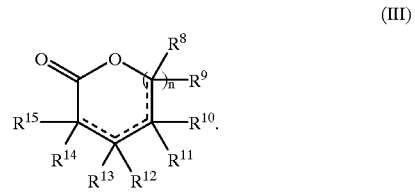

(III)

26 Claims, No Drawings

FRAGRANCE PRECURSORS

FIELD OF THE INVENTION

The present invention relates to fragrance precursors for a fragrant ketone and a fragrant lactone.

BACKGROUND OF THE INVENTION

A principal strategy currently employed in imparting odors to consumer products is the admixing of the fragrance directly into the product. There are, however, several drawbacks to this strategy. The fragrance material can be too volatile and/or too soluble, resulting in fragrance loss during manufacturing, storage, and use. Many fragrance materials are also unstable over time. This again results in loss during storage.

In many consumer products it is desirable for the fragrance to be released slowly over time. Micro-encapsulation and inclusion complexes with cyclodextrins have been used to help decrease volatility, improve stability and provide slow-release properties. However, these methods are often unsuccessful. In addition, cyclodextrins can be too expensive.

Precursors for the delivery of organoleptic compounds, especially for flavors, fragrances, and masking agents, are disclosed in EP-A 0 936 211. This delivery system releases one or more odoriferous compounds upon exposure to light and/or UV irradiation. Using this system in various consumer products leads to a prolonged perception of the fragrant compound(s) to be released.

WO 99/60990 discloses fragrance precursors which release fragrant alcohols, aldehydes, or ketones upon exposure to light. Perfuming compositions containing these fragrance precursors can be used in various consumer products such as detergents, fabric softeners, household products, hair-care products etc.

Many fragrant compounds with odors accepted by the public are lactones. In fragrance compositions these lactones play an important role in imparting the fruity aspects of a perfume. Fragrant lactones are prone to undergo hydrolysis, especially in alkaline products such as detergents, into the hydroxy fatty acids salts, which exhibit enhanced water solubility and to a great extent are washed away in the washing/cleaning process. This results in considerable loss of perfume and in particular the fruity notes. Lactones, especially the aliphatic low molecular weight lactones, are rather volatile compounds. Furthermore, they are water soluble and are, therefore, lost to some extent during the washing/rinsing cycle if introduced directly into detergents.

Therefore, these lactones are of limited use in laundry products, especially detergents.

Cyclic acetals of the formula IV

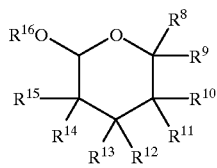

(IV)

where $R^8$ to $R^{15}$ are all H, and $R^{16}$ is the residue of an organic alcohol, which serve as a protective group for alcohols have been described. (Greene, T. W.; Wuts, P. G. M. *Protective Groups in Organic Synthesis*, $2^{nd}$ ed.; John Wiley and Sons: New York, 1991, p31.)

Certain compounds of formula I are known.

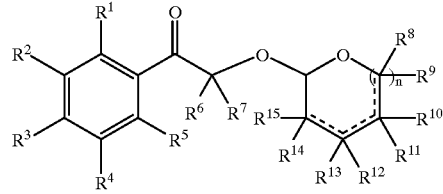

(I)

A compound of formula I where n is 1, $R^8$ is $C_6$, and $R^1$ to $R^7$ as well as $R^9$ to $R^{15}$ are H has been used as an intermediate in a natural product synthesis. (Dixon et al., *Synlett*, 1998, 1093–1095.)

A further compound

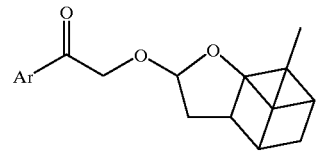

is used as a substrate in a diastereoselective reduction, wherein the cyclic acetal is used as a chiral auxiliary (e.g. Noe et al., *Angew. Chem.* 1988, 100, 1431–1433).

It is known that phenacyl glycosides undergo a Norrish Type II photoreaction leading to gluconolactones and the corresponding aryl ketone (Brunckova and Crich, *Tetrahedron*, 1995, 51, 11945–11952). However, it has not been described or suggested to use such phenacyl acetals as fragrance precursors, which are capable of releasing a fragrant ketone and a fragrant lactone over a prolonged period.

SUMMARY OF THE INVENTION

Accordingly, it would be advantageous to have a fragrance delivery system which is capable of releasing a fragrant compound or compounds in a controlled manner, maintaining a desired smell over a prolonged period of time.

An object of the present invention is to provide fragrance precursors which are stable in an alkaline environment, especially in laundry products.

A further object of the present invention is to provide non-volatile precursors for volatile fragrant lactones.

Also an object of the present invention is to provide fragrance precursors with high substantivity.

A further object of the present invention is to provide fragrance precursors which are activated and cleaved by light.

Also an object of the present invention is to provide fragrance precursors with slow release properties.

One embodiment of the present invention is a fragrance precursor of formula I:

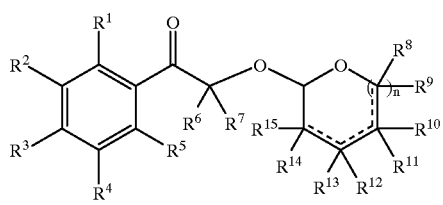

(I)

the dotted lines indicating one or two optional double bonds in the cyclic acetal,
for a fragrant ketone of formula II:

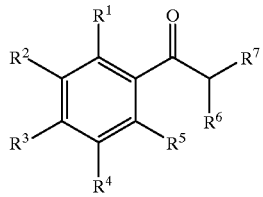

(II)

that forms a fragrant lactone of formula III:

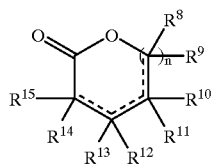

(III)

containing not more than 20 carbon atoms,
wherein
$R^1$ to $R^2$ represent independently H, —$NO_2$, linear or branched $C_1$–$C_6$-alkyl, $C_1$–$C_6$-alkenyl, $C_1$–$C_6$-alkynyl, or $C_1$–$C_4$-alkoxy,
$R^1$ and $R^2$, $R^2$ and $R^3$, $R^3$ and $R^4$, and $R^4$ and $R^5$ may form together one or two aliphatic or aromatic rings, these rings may optionally contain linear or branched $C_1$–$C_4$-alkyl, $C_1$–$C_4$-alkenyl, or $C_1$–$C_4$-alkynyl residues, and these rings and residues may comprise one or more oxygen atoms,
$R^6$ and $R^7$ are independently H, linear or branched $C_1$–$C_6$-alkyl-, $C_1$–$C_6$-alkenyl, or $C_1$–$C_6$-alkynyl, and $R^6$ or $R^7$ may form with either $R^1$ or $R^5$ a carbocyclic ring optionally substituted by an aliphatic residue,
n is either 0 or 1,
$R^8$ to $R^{15}$ are independently H, branched or linear $C_1$–$C_{15}$-alkyl, $C_1$–$C_{15}$-alkenyl, $C_1$–$C_{15}$-alkynyl, or $C_1$–$C_4$-alkoxy, they may form together one or more aliphatic or aromatic rings, these rings may optionally contain branched or linear $C_1$–$C_{10}$-alkyl, $C_1$–$C_{10}$-alkenyl, or $C_1$–$C_{10}$-alkynyl residues, and these rings and residues may comprise one or more oxygen atoms, or
$R^8$ and $R^9$ together; $R^{10}$ and $R^{11}$ together; $R^{12}$ and $R^{13}$ together; or $R^{14}$ and $R^{15}$ together represent H, branched or linear $C_1$–$C_{15}$-alkyl, $C_1$–$C_{15}$-alkenyl, $C_1$–$C_{15}$-alkynyl or $C_1$–$C_4$-alkoxy when the ring carbon atom supporting these groups is unsaturated.

Another embodiment of the present invention is a compound of formula I:

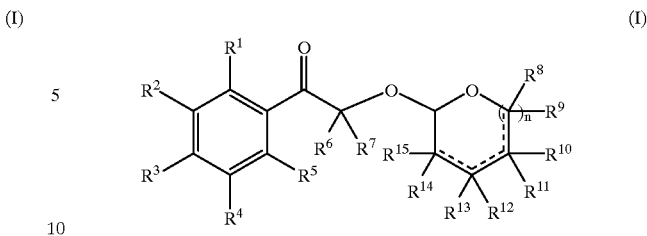

(I)

the dotted lines indicating one or two double bonds in the ring of the cyclic acetal,
wherein
$R^1$ to $R^5$ represent independently H, —$NO_2$, linear or branched $C_1$–$C_6$-alkyl, $C_1$–$C_6$-alkenyl, $C_1$–$C_6$-alkynyl, or $C_1$–$C_4$-alkoxy,
$R^1$ and $R^2$, $R^2$ and $R^3$, $R^3$ and $R^4$, and $R^4$ and $R^5$ may form together one or two aliphatic or aromatic rings, these rings may optionally contain substituted or unsubstituted $C_1$–$C_4$-alkyl, $C_1$–$C_4$-alkenyl, or $C_1$–$C_4$-alkynyl residues, and may comprise one or more oxygen atoms,
$R^6$ and $R^7$ are independently H, linear or branched $C_1$–$C_6$-alkyl, $C_1$–$C_6$-alkenyl, $C_1$–$C_6$-alkynyl, and $R^6$ or $R^7$ may form with either $R^1$ or $R^5$ a substituted or unsubstituted carbocyclic ring,
n is either 0 or 1,
$R^8$ to $R^{15}$ are independently H, branched or linear $C_1$–$C_{15}$-alkyl, $C_1$–$C_{15}$-alkenyl, $C_1$–$C_{15}$-alkynyl, or $C_1$–$C_4$-alkoxy,
they may form together one ore more aliphatic or aromatic rings, these rings may optionally contain branched or linear $C_1$–$C_{10}$-alkyl, $C_1$–$C_{10}$-alkenyl, or $C_1$–$C_{10}$-alkynyl residues, and the above rings and residues may comprise one or more oxygen atoms, and
a lactone of formula III:

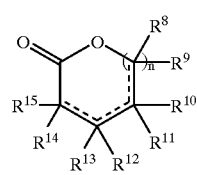

(III)

which contains not more than 20 carbon atoms.
A further embodiment of the present invention is a compound of formula I:

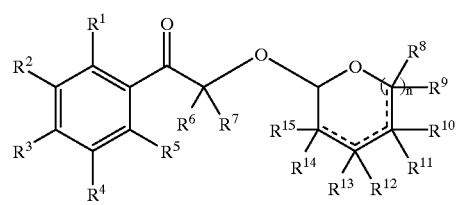

(I)

wherein
the ring of the acetal is saturated,
$R^1$ to $R^5$ represent independently H, —$NO_2$, linear or branched $C_1$–$C_6$-alkyl, $C_1$–$C_6$-alkenyl, $C_1$–$C_6$-alkynyl, or $C_1$–$C_4$-alkoxy,
$R^1$ and $R^2$, $R^2$ and $R^3$, $R^3$ and $R^4$, and $R^4$ and $R^5$ may form together one or two aliphatic or aromatic rings, these rings may optionally contain substituted or unsubstituted $C_1$–$C_4$-alkyl, $C_1$–$C_4$-alkenyl, or $C_1$–$C_4$-alkynyl residues, and may comprise one or more oxygen atoms, $R^6$ and $R^7$ are independently H, linear or branched $C_1$–$C_6$-alkyl, $C_1$–$C_6$-alkenyl, or $C_1$–$C_6$-alkynyl, and $R^6$ or $R^7$ may form with either $R^1$ or $R^5$ a substituted or unsubstituted carbocyclic ring, n is 0, $R^8$ to $R^{15}$ are independently H, branched or linear $C_1$–$C_{15}$-alkyl, $C_1$–$C_{15}$-alkenyl, $C_1$–$C_{15}$-alkynyl, or $C_1$–$C_4$-alkoxy, they may form together one aliphatic or aromatic ring, and the ring may optionally contain branched or linear $C_1$–$C_{10}$-alkyl, $C_1$–$C_{10}$-alkenyl, or $C_1$–$C_{10}$-alkynyl residues, and the above rings and residues may comprise one or more oxygen atoms, and a lactone of formula III:

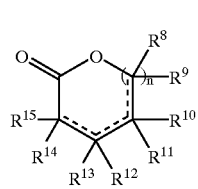

(III)

which contains not more than 20 carbon atoms.

Another embodiment of the present invention is a compound of formula I:

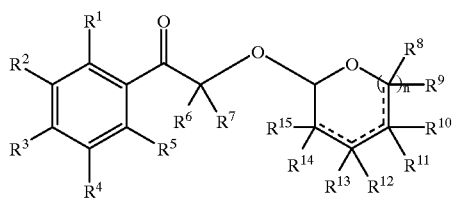

(I)

wherein
the ring of the acetal is saturated, $R^1$ to $R^5$ represent independently H, —$NO_2$, linear or branched $C_1$–$C_6$-alkyl, $C_1$–$C_6$-alkenyl, $C_1$–$C_6$-alkynyl, or $C_1$–$C_4$-alkoxy, $R^1$ and $R^2$, $R^2$ and $R^3$, $R^3$ and $R^4$, and $R^4$ and $R^5$ may form together one or two aliphatic or aromatic rings, these rings may optionally contain substituted or unsubstituted $C_1$–$C_4$-alkyl, $C_1$–$C_4$-alkenyl, or $C_1$–$C_4$-alkynyl residues, and may comprise one or more oxygen atoms, $R^6$ and $R^7$ are independently H, linear or branched $C_1$–$C_6$-alkyl, $C_1C_6$-alkenyl, or $C_1$–$C_6$-alkynyl, and $R^6$ or $R^9$ may form with either $R^1$ or $R^5$ a substituted or unsubstituted carbocyclic ring, n is 1, $R^8$ to $R^{15}$ are independently H, branched or linear $C_1$–$C_{15}$-alkyl, $C_1$–$C_{15}$-alkynyl, or $C_1$–$C_4$-alkoxy, they may form together one or more aliphatic or aromatic rings, these rings may optionally contain branched or linear $C_1$–$C_{10}$-alkyl, $C_1$–$C_{10}$-alkenyl, or $C_1$–$C_{10}$-alkynyl residues, and the above rings and residues may comprise one or more oxygen atoms, with the proviso that compounds
wherein
all of $R^8$ to $R^{15}$ are H, or
all of $R^{10}$ to $R^{15}$ are H and either $R^8$ is $C_6$ and $R^9$ is H or $R^9$ is $C_6$ and $R^8$ is H
are excluded, and a lactone of formula III:

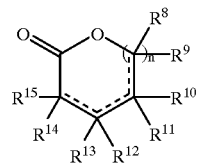

(III)

which contains not more than 20 carbon atoms.

A further embodiment of the present invention is a perfumed product comprising a fragrance precursor of formula I:

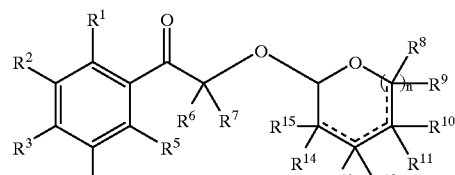

(I)

the dotted lines indicating one or two optional double bonds in the cyclic acetal, that forms fragrant ketone of formula II:

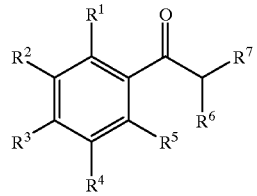

(II)

and a fragrant lactone of formula III:

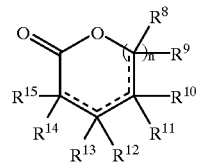

(III)

containing not more than 20 carbon atoms,
wherein $R^1$ to $R^5$ represent independently H, —$NO_2$, linear or branched $C_1$–$C_6$-alkyl, $C_1$–$C_6$-alkenyl, $C_1$–$C_6$-alkynyl, or $C_1$–$C_4$-alkoxy, $R^1$ and $R^2$, $R^2$ and $R^3$, $R^3$ and $R^4$, and $R^4$ and $R^5$ may form together one or two aliphatic or aromatic rings, these rings may optionally contain linear or branched $C_1$–$C_4$-alkyl, $C_1$–$C_4$-alkenyl, or $C_1$–$C_4$-alkynyl residues, and these rings and residues may comprise one or more oxygen atoms, $R^6$ and $R^7$ are independently H, linear or branched $C_1$–$C_6$-alkyl-, $C_1$–$C_6$-alkenyl, or $C_1$–$C_6$-alkynyl, and $R^6$ or $R^7$ may form with either $R^1$ or $R^5$ a carbocyclic ring optionally substituted by an aliphatic residue, n is either 0 or 1, $R^8$ to $R^{15}$ are independently H, branched or linear $C_1$–$C_{15}$-alkyl, $C_1$–$C_{15}$-alkenyl, $C_1$–$C_{15}$-alkynyl, or $C_1$–$C_4$-alkoxy, they may form together one or more aliphatic or aromatic rings, these rings may optionally contain branched or linear $C_1$-$C_{10}$-alkyl, $C_1$–$C_{10}$-alkenyl, or $C_1$–$C_{10}$-alkynyl residues, and these rings and residues may comprise one or more oxygen atoms.

Another embodiment of the present invention is a perfumed product according to claim 21 wherein the perfumed product is selected from the group consisting of laundry compositions, cleaning products, body care products, and personal care products.

Another embodiment of the present invention is a process for providing a fragrance to a substrate comprising:
(a) treating a substrate with a perfumed product comprising a fragrance precursor of formula I:

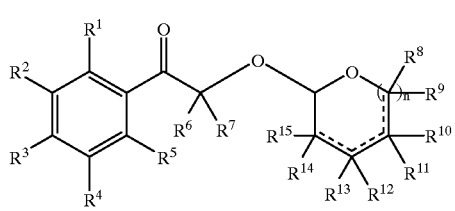

(I)

the dotted lines indicating one or two optional double bonds in the cyclic acetal,
wherein
$R^1$ to $R^5$ represent independently H, —$NO_2$, linear or branched $C_1$–$C_6$-alkyl, $C_1$–$C_6$-alkenyl, $C_1$–$C_6$-alkynyl, or $C_1$–$C_4$-alkoxy,
$R^1$ and $R^2$, $R^2$ and $R^3$, $R^3$ and $R^4$, and $R^4$ and $R^5$ may form together one or two aliphatic or aromatic rings, these rings may optionally contain linear or branched $C_1$–$C_4$-alkyl, $C_1$–$C_4$-alkenyl, or $C_1$–$C_4$-alkynyl residues, and these rings and residues may comprise one or more oxygen atoms,
$R^6$ and $R^7$ are independently H, linear or branched $C_1$–$C_6$-alkyl-, $C_1$–$C_6$-alkenyl, or $C_1$–$C_6$-alkynyl, and $R^6$ or $R^7$ may form with either $R^1$ or $R^5$ a carbocyclic ring optionally substituted by an aliphatic residue,
n is either 0 or 1,
$R^8$ to $R^{15}$ are independently H, branched or linear $C_1$–$C_{15}$-alkyl, $C_1$–$C_{15}$-alkenyl, $C_1$–$C_{15}$-alkynyl, or $C_1$–$C_4$-alkoxy, they may form together one or more aliphatic or aromatic rings, these rings may optionally contain branched or linear $C_1$-$C_{10}$-alkyl, $C_1$–$C_{10}$-alkenyl, or $C_1$–$C_{10}$-alkynyl residues, and these rings and residues may comprise one or more oxygen atoms; and
(b) allowing the compound of formula I to be cleaved to form a fragrant ketone of formula II:

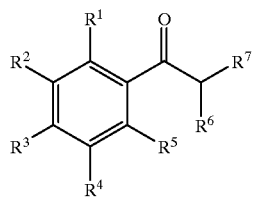

(II)

and a fragrant lactone of formula III:

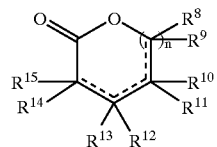

(III)

containing not more than 20 carbon atoms.

A further embodiment of the present invention is a process for providing a perfumed product comprising:
(a) forming a mixture by combining a base material with a compound according to formula I:

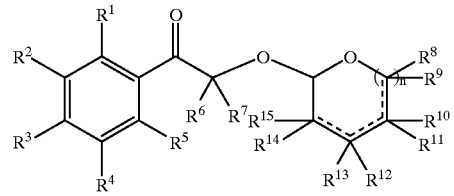

(I)

the dotted lines indicating one or two optional double bonds in the cyclic acetal, that forms fragrant ketone of formula II:

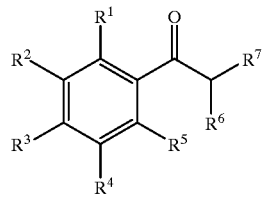

(II)

and a fragrant lactone of formula III:

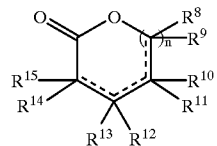

(III)

containing not more than 20 carbon atoms,
wherein
$R^1$ to $R^5$ represent independently H, —$NO_2$, linear or branched $C_1$–$C_6$-alkyl, $C_1$–$C_6$-alkenyl, $C_1$–$C_6$-alkynyl, or $C_1$–$C_4$-alkoxy,
$R^1$ and $R^2{}_1$, $R^2$ and $R^3$, $R^3$ and $R^4{}_1$, and $R^4$ and $R^5$ may form together one or two aliphatic or aromatic rings, these rings may optionally contain linear or branched $C_1$–$C_4$-alkyl, $C_1$–$C_4$-alkenyl, or $C_1$–$C_4$-alkynyl residues, and these rings and residues may comprise one or more oxygen atoms,
$R^6$ and $R^7$ are independently H, linear or branched $C_1$–$C_6$-alkyl-, $C_1$–$C_6$-alkenyl, or $C_1$–$C_6$-alkynyl, and $R^6$ or $R^7$ may form with either $R^1$ or $R^5$ a carbocyclic ring optionally substituted by an aliphatic residue,
n is either 0 or 1,
$R^8$ to $R^{15}$ are independently H, branched or linear $C_1$–$C_{15}$-alkyl, $C_1$–$C_{15}$-alkenyl, $C_1$–$C_{15}$-alkynyl, or $C_1$–$C_4$-alkoxy, they may form together one or more aliphatic or aromatic rings, these rings may optionally contain branched or linear $C_1$-$C_{10}$-alkyl, $C_1$-$C_{10}$-alkenyl, or $C_1$-$C_{10}$-alkynyl residues, and these rings and residues may comprise one or more oxygen atoms; and (b) forming a perfumed product from the mixture.

DETAILED DESCRIPTION OF THE INVENTION

The present invention relates to fragrance precursors of formula I

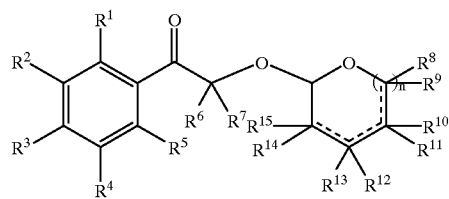

(I)

wherein the dotted lines indicate the location of one or two optional double bonds in the cyclic acetal, which precursors upon exposure to light, and in particular daylight, release a fragrant ketone of formula II

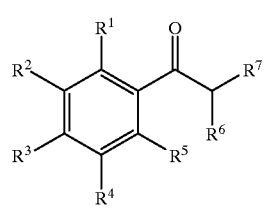

(II)

and a fragrant lactone of formula III

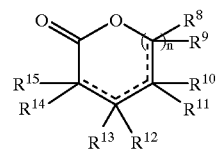

(III)

containing not more than 20 carbon atoms, wherein $R^1$ to $R^5$ represent independently H, —$NO_2$, branched or linear $C_1$-$C_6$-alkyl, $C_1$-$C_6$-alkenyl, $C_1$-$C_6$-alkynyl, or $C_1$-$C_4$-alkoxy, $R^1$ and $R^2$, $R^2$ and $R^3$, $R^3$ and $R^4$, and $R^4$ and $R^5$ may form together one or two aliphatic or aromatic rings, these rings may optionally contain branched or linear $C_1$-$C_4$-alkyl, $C_1$-$C_4$-alkenyl, or $C_1$-$C_4$-alkynyl residues, and the above rings and residues may comprise one or more oxygen atoms, $R^6$ and $R^7$ are independently H, branched or linear $C_1$-$C_6$-alkyl, $C_1$-$C_6$-alkenyl, or $C_1$-$C_6$-alkynyl, and $R^6$ or $R^7$ may form with either $R^1$ or $R^5$ a carbocyclic ring optionally substituted by an aliphatic residue, n is 0 or 1, $R^8$ to $R^{15}$ are independently H, branched or linear $C_1$-$C_{15}$-alkyl, $C_1$-$C_{15}$-alkenyl, $C_1$-$C_{15}$-alkynyl, or $C_1$-$C_4$-alkoxy, and they may form together one or more aliphatic or aromatic rings, these rings may optionally contain branched or linear $C_1$-$C_{10}$-alkyl, $C_1$-$C_{10}$-alkenyl or $C_1$-$C_{10}$-alkynyl residues, and the above rings and residues may comprise one or more oxygen atoms, or $R^8$ and $R^9$ together; $R^{10}$ and $R^{11}$ together; $R^{12}$ and $R^{13}$ together; or $R^{14}$ and $R^{15}$ together represent H, branched or linear $C_1$-$C_{15}$-alkyl, $C_1$-$C_{15}$-alkenyl, $C_1$-$C_{15}$-alkynyl or $C_1$-$C_4$-alkoxy when the ring carbon atom supporting these groups is unsaturated, and branched carbon chains also comprise multiple branched chains.

The present invention also relates to compounds of formula I.

The fragrance precursors of formula I release, upon exposure to light, volatile fragrant lactones of formula III and fragrant ketones of formula II. Since the precursors of the invention are stable in alkaline environment and show high substantivity, they are excellently adapted for detergent and laundry use.

The fragrance precursors of the present invention are slowly cleaved when exposed to light, in particular daylight. Upon absorption of energy from the light, the phenacyl acetals undergo a Norrish Type II photoreaction which leads to the release of a fragrant ketone of formula II and a fragrant lactone of formula III.

The release of the above mentioned fragrant compounds occurs, for example, upon exposure to sunlight penetrating through ordinary windows and therefore, not being particularly rich in UV irradiation. Obviously, upon exposure to bright sunlight, in particular outdoors, the release of the fragrant compounds of formula II and III will occur faster and to a greater extent than upon exposure to room light inside a building. The cleavage of the precursors of the present invention can also be initiated by an appropriate lamp, for example a sun tanning lamp.

The photoreaction of the fragrance precursors of formula I begins with the absorption of light by the keto-group followed by abstraction of the acetal-H atom and subsequent cleavage of the resulting 1,4-diradical (Scheme A). It has been found that the aromatic residue of the fragrance precursors plays an important role in this photoreaction as it influences the absorption maximum $\lambda_{max}$ of the keto-group. Therefore, the cleavage properties of the fragrance precursors can be modified by variation of the substituents $R^1$ to $R^5$.

Scheme A

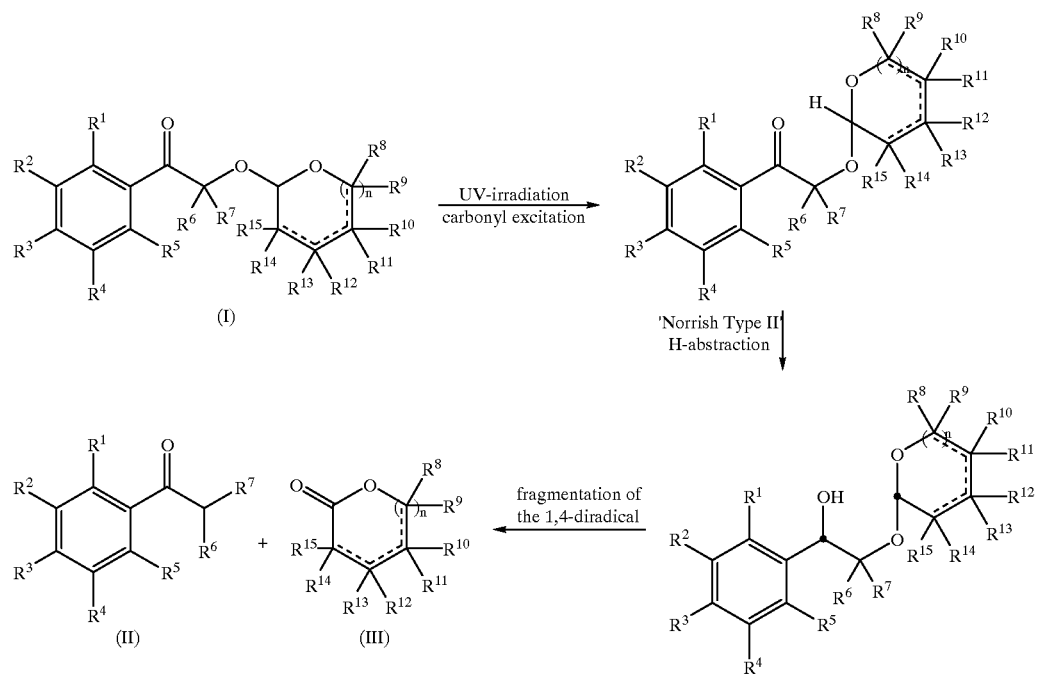

Examples of ketones of formula II are: acetanisole (1-(4-methoxyphenyl)-ethanone) (Givaudan Roure (International) SA, Vernier, Switzerland), acetophenone (1-phenyl-ethanone) (Haarmann & Reimer GmbH, Germany), CRYSOLIDE® (4-acetyl-6-tert-butyl-1,1-dimethyl-indan) (Givaudan Roure (International) SA, Vernier, Switzerland), Dimethyl acetophenone (1-(2,4-dimethylphenyl)-ethanone) (Fluka AG, Buchs, Switzerland), FIXOLIDE® (1-(5,6,7,8-tetrahydro-3',5',5',6',8',8'-hexamethyl-2-naphthalenyl)-ethanone) (Givaudan Roure (International) SA, Vernier, Switzerland), FLORANTONE T® (1-(5,6,7,8-tetrahydro-2-naphthalenyl)-ethanone) (Takasago Perfumery Co., Japan), GRASSENONE 34® (3-methyl-1-(4-methylphenyl)-4-hexen-1-one) (Keemia Institute, Tallin USSR), isopropylindanone (2-(1-methylethyl)-indanone) (Givaudan Roure (International) SA, Vernier, Switzerland), LAVONAX® (1-phenyl-4-penten-1-one) (International Flavors & Fragrances, USA), Musk F (5-acetyl-1,1,2,3,3-pentamethyl-indane) (CNNP), MUSK KETONE® (4-tert-butyl-3,5-dinitro-2,6-dimethyl-acetophenone) (Givaudan Roure (International) SA, Vernier, Switzerland), NOVALIDE® (1,6,7,8-tetrahydro-1',4',6',6',8',8'-hexamethyl-indacen-3(2H)-one) (Givaudan Roure (International) SA, Vernier, Switzerland), ORANGER CRYSTALS® (1-(2-naphthalenyl)-ethanone) (Givaudan Roure (International) SA, Vernier, Switzerland), ORINOX® (1-(4-(1,1-dimethylethyl)-2,6-dimethylphenyl)-ethanone) (Polak's Frutal Works BV, Netherlands), PHANTOLIDE® (1-(2,3-dihydro-1',1',2',3',3',6'-hexamethyl-1H-inden-5-yl-ethanone) (Polak's Frutal Works BV, Netherlands), pro-piophenone (1-phenyl-propanone) (Haarmann & Reimer GmbH, Germany), TRASEOLIDE 100® (1-(2,3-dihydro-1',1',2',6'-tetramethyl-3-(1-methylethyl)-1H-inden-5-yl-ethanone) (Quest International, Netherlands), VERNO-LIDE® (1-(5,6,7,8-tetrahydro-3',5',5',8',8'-pentamethyl-2-naphthalenyl)-ethanone) (Givaudan Roure (International) SA, Vernier, Switzerland), VERSALIDE® (1-(5,6,7,8-tetrahydro-3'-ethyl-5',5',8',8'-tetramethyl-2-naphthalenyl)-ethanone) (Givaudan Roure (International) SA, Vernier, Switzerland), and VITALIDE® (1-(hexa-hydrodimethyl-1H-benzindenyl)-ethanone) (Takasago Perfumery, Japan).

The above list is illustrative, and the present invention relates to many other fragrant ketones of formula II.

Additional fragrant ketones of formula II are described in, e.g., "Perfume and Flavor Chemicals," S. Arctander Ed. , Vol. I & II, Allured Publishing Corporation, Carol Stream, USA, 1994, and in "Common Fragrance and Flavor Materials," K. Bauer, D. Garbe and H. Surburg, Eds., Wiley-VCH, 3$^{rd}$ Edition, Weinheim, 1997.

Fragrant lactones of formula III, represent an important class of perfumery raw materials and include compounds of a vast structural variety. Fragrant lactones of formula III contribute to the odor and aroma of various fruits and are known to be useful ingredients for the formulation of perfumes or perfumed articles.

Most of the lactones of formula III are gamma-lactones wherein n is 0. They are derived from gamma-hydroxy-carboxylic acids, and examples of such lactones of formula III include: gamma-valerolactone, gamma-octalactone, PRUNOLIDE® (gamma nonalactone) (Givaudan Roure (International) SA, Vernier, Switzerland), gamma-decalactone, PEACH PURE® (gamma-undecalactone) (Givaudan Roure (International) SA, Vernier, Switzerland), gamma-dodecalactone, 5-(3Z-hexenyl)-dihydro-2(3H)-furanone, and 5-(1,5-dimethyl-4-hexenyl)-dihydro-2(3H)-furanone.

Alpha-monosubstituted gamma-lactones of formula III wherein n is 0 are, for example, 2-heptylbutyrolactone and 2-hexylbutyrolactone.

Bisubstituted gamma-lactones of formula III wherein n is 0 are, for example, Lactone of CIS-JASMONE® (5-(3Z-hexenyl)-dihydro-5-methyl-2(3H)-furanone) (Bedoukian Inc., USA), LACTOJASMONE® (5-hexyl-dihydro-5-methyl-2(3H)-furanone) (Haarmann & Reimer GmbH, Germany), Whiskey Lactone (Fontarome Chemical Inc., USA), 4-methyl-5-pentyl-dihydro-2(3H)-furanone, and 3-acetyl-5-butyl-dihydro-2(3H)-furanone.

Bisubstituted spiro-bicyclic gamma-lactones of formula III wherein n is 0 are, for example, LAITONE® {8-(1- methylethyl)-1-oxaspiro(4.5)-decan-2-one} (Givaudan Roure (International) SA, Vernier, Switzerland), ETHYL LAITONE® {8-ethyl-1-oxaspiro(4.5)-decan-2-one} (Givaudan Roure (International) SA, Vernier, Switzerland), and METHYL LAITONE® {8-methyl-1-oxaspiro(4.5)-decan-2-one} (Givaudan Roure (International) SA, Vernier, Switzerland).

Another important class of the lactones of formula III are the delta-lactones wherein n is 1. They are derived from the delta-hydroxy-carboxylic acids and examples for such lactones of formula III include: delta-hexalactone, delta-heptalactone, delta-octalactone, delta-nonalactone, delta-decalactone, delta-undecalactone, delta-dodecalactone and delta-tetradecalactone. Further examples comprise Jasmolactone {6-(3E-pentenyl)-tetrahydro (2H)pyran-2-one} (Firmenich S. A., Switzerland), Jasmolactone Extra C {6-(3Z-hexenyl)-tetrahydro(2H)pyran-2-one} (Bedoukian Inc., USA), and 6-(2Z-pentenyl)-tetrahydro (2H)pyran-2-one.

Multiple-substituted monocyclic lactones of formula III are the delta-lactones wherein n is 1. Such lactones of formula III are, for example, 4,4,6-trimethyltetrahydropyran-2-one and 5-butyl-5-ethyl-tetrahydropyran-2-one.

Multiple-substituted polycyclic lactones of formula III are the delta-lactones wherein n is 1. Such lactones of formula III are, for example, FLOREX® (6- or 7-ethylideneoctahydro-5,8-methano(2H)-1-benzopyran-2-one) (Firmenich S. A., Switzerland), LACTOSCATONE® (hexahydro-3,5,5-trimethyl-3,8a-ethano(8aH)-1-benzopyran-2(3H)one) (DRAGOCO Gerberding & Co. AG, Germany) (Dragoco), Coumarin, Dihydrocoumarin (Givaudan Roure (International) SA, Vernier, Switzerland), and Octahydrocoumarin.

Some of the lactones of formula III described above, which are of pleasant odor, are particularly volatile. This is especially true for low molecular weight lactones that are substituted by aliphatic chains exhibiting typical fruity odors.

The fragrance precursors of the present invention are not, or are only slightly, volatile. The fragrant ketones of formula II and the fragrant lactones of formula III are released only upon exposure to light, especially daylight. The photochemical cleavage releases, over days and weeks, perceptible amounts of the fragrant compounds. The period depends, inter alia, on the amount or concentration of the precursor applied, the duration of exposure to light, its intensity, and its wavelength.

As used herein, the term "precursor" means a compound of formula I that is odorless until it undergoes photochemical cleavage to release fragrant compounds of formulae II and III.

Today's consumers select a certain product not only based on performance but also based on the odor. From the foregoing it is evident that systems for introducing a variety of fragrance accords to products having alkaline pH are desirable. The fragrance precursors of the present invention have the advantage that they are not or only slightly volatile and chemically stable in consumer products having alkaline and neutral pH. A precursor of formula I added to a powder detergent, is stable in the detergent powder throughout storage. During the washing cycle (alkaline pH) and the rinsing cycle (neutral pH) the precursor is deposited on the fabric surface. It is only upon exposure of the fabric to light, for example during line drying in the sun, that the release of the fragrant ketones of formula II and the fragrant lactones of formula III is started.

The fragrance precursors of formula I have the advantage that they have good substantivity on different substrates, especially on fabrics. Furthermore, the precursors are not or only slightly volatile, thus no loss occurs during storage. With the precursors of the present invention highly volatile lactones of formula III with low substantivity are successfully applied to achieve a long lasting pleasant odor. The volatile lactones are produced in situ after application of the precursors of formula I onto a fabric during the washing cycle.

As used herein, the term "substrate" means a fabric, a hard surface, skin, hair, or any other surface upon which it would be desirable to impart a fragrance.

In the precursors of the invention, the moiety derived from a fragrant ketone of formula II has three advantages: it introduces stability to the precursors of formula I, it introduces substantivity to the precursors of formula I and upon activation by light it exhibits fragrant properties.

The fragrance precursors of the present invention are advantageously prepared by two methods. Both methods use an α-hydroxy-ketone as starting material. The α-hydroxy-ketone is prepared by bromination of the corresponding fragrant ketone followed by sodium formate treatment and subsequent hydrolysis as shown in scheme I:

Scheme I

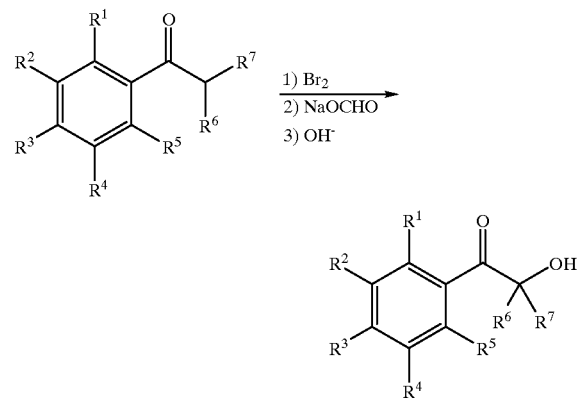

Then according to the first method, the α-hydroxy-ketone intermediate is reacted under acid conditions with a cyclic vinyl ether to the desired precursor of formula I. The cyclic vinyl ether is obtained from the corresponding lactone after reduction to the lactol, followed by acetylation and thermal elimination of acetic acid. For this method, either $R^{14}$ or $R^{15}$ needs to be H. The synthesis is illustrated in scheme II:

Scheme II

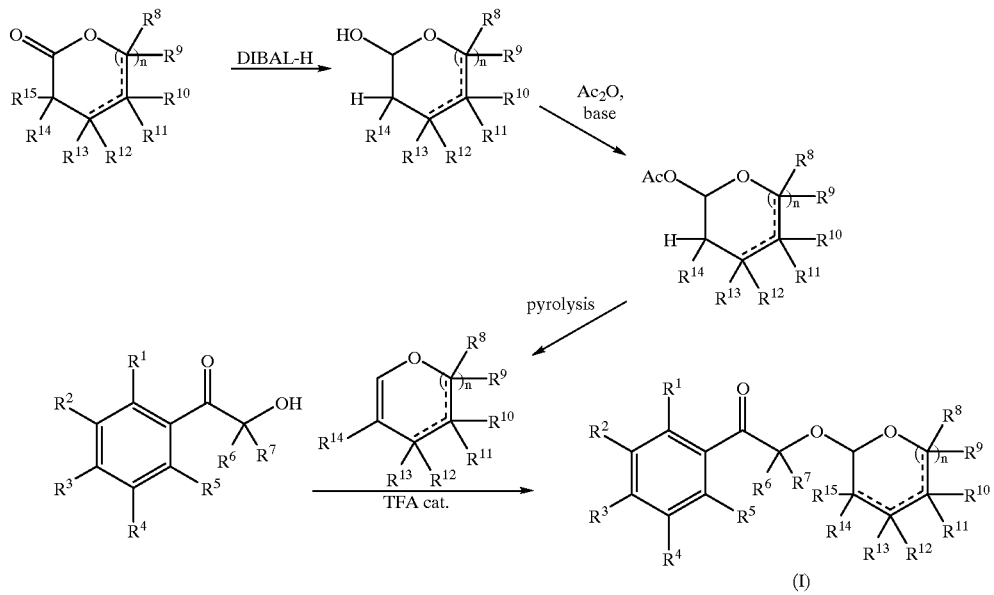

DIBAL-H is diisobutylaluminium hydride. TFA is trifluoracetic acid. The abbreviation "cat." means the compound is used in a catalytic amount.

According to the second method, the α-hydroxy-ketone is reacted under slightly basic conditions with the aforementioned lactol acetate. This method is particularly suitable for lactones where both $R^{14}$ and $R^{15}$ are not H. The synthesis via this route is illustrated in scheme III:

Scheme III

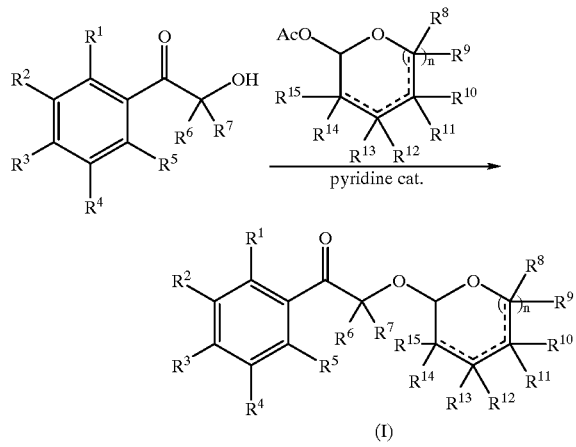

Preferred precursors of the present invention are compounds releasing a lactone of formula III wherein n is 0, $R^{10}$ is an aliphatic residue having 1 to 15 carbon atoms, and $R^{11}$ to $R^{15}$ are H. More preferred precursors are those releasing a lactone derived from gamma-hydroxy fatty acids having 4 to 14 carbon atoms.

Other preferred precursors include compounds wherein n is 0, one substituent of $R^{11}$ to $R^{15}$ is an aliphatic residue having 1 to 15 carbon atoms, and the remaining residues from $R^{11}$ to $R^{15}$ are H. More preferred compounds are those releasing a lactone wherein the aliphatic residue is $R^{15}$ and has 1 to 10 carbon atoms.

Other preferred precursors include compounds wherein n is 0, two or more substituents of $R^{10}$ to $R^{15}$ are aliphatic residues having 1 to 15 carbon atoms, and the remaining residues from $R^{10}$ to $R^{15}$ are H. More preferred compounds are those wherein $R^{10}$ and $R^{11}$ are aliphatic residues having 1 to 10 carbon atoms.

Other preferred precursors include compounds wherein n is 0 and two or more substituents of $R^{10}$ to $R^{15}$ are residues having 1 to 15 carbon atoms and form together one or more carbocyclic ring(s), which may optionally be substituted with one or more aliphatic residue(s) having 1 to 10 carbon atoms. More preferred compounds are spirocyclic structures wherein $R^{10}$ to $R^{11}$ form together a carbocyclic ring which is further substituted with one or more aliphatic residues having 1 to 10 carbon atoms.

Other preferred precursors of the present invention are compounds releasing a lactone of formula III wherein n is 1, $R^8$ is an aliphatic residue having 1 to 15 carbon atoms, and $R^9$ to $R^{15}$ are H. More preferred precursors are those releasing a lactone derived from delta-hydroxy fatty acids having 5 to 14 carbon atoms.

Other preferred precursors include compounds wherein n is 1, two or more substituents of $R^8$ to $R^{15}$ are aliphatic residues having 1 to 15 carbon atoms, and the remaining residues from $R^8$ to $R^{15}$ are H. More preferred compounds are 4,4,6-trimethyltetrahydropyran-2-one and 5-butyl-5-ethyl-tetrahydropyran-2-one.

Other preferred precursors include compounds wherein n is 1 and at least two substituents of $R^8$ to $R^{15}$ are residues having 1 to 15 carbon atoms and form together one or more carbocyclic ring(s), which may optionally be substituted with one or more aliphatic residues having 1 to 10 carbon atoms. More preferred compounds are FLOREX® (6- or 7-ethylideneoctahydro-5,8-methano(2H)-1-benzopyran-2-one) (Firmenich S. A., Switzerland), LACTOSCATONE® (hexahydro-3,5,5-trimethyl-3,8a-ethano(8aH)-1-benzopyran-2(3H)one) (DRAGOCO Gerberding & Co. AG, Germany) (Dragoco), Coumarin, Dihydrocoumarin (Givaudan Roure (International) SA, Vernier, Switzerland), and Octahydrocoumarin.

Other preferred precursors include compounds wherein at least one of the residues $R^6$ or $R^7$ is H. More preferred are compounds wherein $R^6$ and $R^7$ are H. Upon cleavage of these precursors a fragrant ketone of formula II is released wherein said ketone is an aryl methyl ketone.

Other preferred precursors include compounds wherein $R^6$ and $R^7$ are H and $R^1$ to $R^5$ represent independently hydrogen, —$NO_2$, linear or branched $C_1$–$C_6$ alkyl, alkenyl, alkynyl, and $C_1$–$C_4$ alkoxy. More preferred compounds are those releasing a fragrant ketone of formula II wherein the fragrant ketone is selected from the group 1-phenyl-ethanone, 2,4-dimethylphenyl-ethanone, 1-(4-(1,1-dimethylethyl)-2,6-dimethylphenyl)-ethanone, 1-(4-tert-butyl-3,5-dinitro-2,6-dimethyl)-ethanone, and 1-(4-methoxyphenyl)-ethanone.

Other preferred precursors include compounds wherein $R^1$ and $R^2$, $R^2$ and $R^3$, $R^3$ and $R^4$, and $R^4$ and $R^5$ form together one or two ring(s), which is (are) aliphatic and/or aromatic. These rings may optionally contain substituted or unsubstituted $C_1$–$C_4$ alkyl, alkenyl, or alkynyl residues, and may contain one or more oxygen atoms. More preferred compounds are those releasing a fragrant ketone of formula II wherein the fragrant ketone is selected from the group 1-(2-naphtalenyl)-ethanone, 4-acetyl-6-tert-butyl-1,1-dimethyl-indan, 1-(5,6,7,8-tetrahydro-3',5',5',6',8',8'-hexamethyl-2-naphthalenyl)-ethanone, 1-(5,6,7,8-tetrahydro-3',5',5',8',8'-pentamethyl-2-naphthalenyl)-ethanone, 1-(5,6,7,8-tetrahydro-3'-ethyl-5',5',8',8'-tetramethyl-2-naphthalenyl)-ethanone, 1-(2,3-dihydro-1',1',2',3',3',6'-hexamethyl-1H-inden-5-yl)-ethanone, 1-(2,3-dihydro-1',1',2',6'-tetramethyl-3-(1-methylethyl)-1H-inden-5-yl-ethanone), 5-acetyl-1,1,2,3,3-pentamethyl-indane, and 1-(5,6,7,8-tetrahydro-2-naphthalenyl)-ethanone.

Because the compounds of formula I, upon exposure to light, are cleaved and provide a fragrant ketone of formula II and a fragrant lactone of formula III, they permit the development of useful consumer products with enhanced fragrant properties, especially having long lasting pleasant odor. Therefore, the present invention also relates to products containing the fragrant precursors.

The fragrance precursors of the present invention can be used in any product in which a prolonged and defined release of the above mentioned fragrant compounds is desired. Therefore, these precursors are especially useful in functional and fine perfumery, particularly in products which are exposed to sunlight, during or after application.

The compounds of the present invention also can act as fragrance precursors in fine fragrances, industrial, institutional, home, and personal care products. To this end, the compounds of the present invention are incorporated, e.g. by mixing, stirring or other conventional mixing process, into a suitable base material from which functional and fine fragrances, industrial, institutional, home, and personal care products are made. Such base materials are conventional and well known to those skilled in the art. Industrial, institutional, and home cleaning products to which the fragrance precursors can be added include all kinds of detergents, window cleaners, hard surface cleaners, all purpose cleaners, and furniture polishes. The products can be in the form of liquids or solids, such as powders or tablets. Fabrics and surfaces treated with a product containing a fragrance precursor of the present invention will release a fresh and clean odor upon exposure to light much longer than when cleaned with a conventional cleaner. Fabrics or cloths washed with such detergents will release the fragrant compounds even after having been stored for weeks in a dark place, e.g., a wardrobe.

The precursors of the present invention are also useful for application in all kinds of body care products. Especially interesting products are hair care products, for example shampoos, conditioners, and hairsprays and skin care products such as cosmetic products and especially sun protection products.

The above mentioned products are of course only illustrative and non-limiting. Many other products to which the precursors of the present invention may be added include soaps, bath and shower gels, deodorants, and even perfumes and colognes.

The fragrance precursors of the present invention can be used alone or in combination with other fragrance ingredients, solvents or adjuvants known to those skilled in the art. Such ingredients are described, for example, in "Perfume and Flavor Chemicals," S. Arctander, Ed., Vol. I & II, Allured Publishing Corporation, Carol Stream, USA, 1994 and include fragrance compounds of natural or synthetic origin and essential oils of natural products.

The amount of precursor of formula I to be incorporated into the various above-mentioned products will vary within a wide range. The amounts depend on the nature of the fragrant compounds to be released, the nature of the product to which the precursors are added, and the desired olfactory effect. The amounts used also depend on the co-ingredients in a given composition when the precursors of the present invention are used in admixture with perfuming co-ingredients, solvents, or adjuvants. Typical concentrations of the precursors are in the range of 0.01% to 5% by weight of the products.

The following examples are provided to further illustrate various aspects of the present invention. These examples are illustrative only and are not intended to limit the scope of the invention in any way.

EXAMPLES

In the examples that follow, the following chemicals were obtained from commercial sources: bromo-acetonaphtone, bromo-acetanisole, sodium formate, diisobutyl-aluminum hydride (solution in hexanes), JASMOLACTONE®, PEACH PURE®, METHYL LAITONE®, acetic anhydride, triethylamine, pyridine, trifluoracetic acid. α-Bromo-Fixolide was prepared from FIXOLIDE® according to R. M. Cowper, L. H. Davidson, *Org. Synth. Coll. Vol. II,* 1943, 480–481.

NMR: values of coupling constants J are given in Hertz (Hz).

Example 1

Preparation of Cyclic Phenacyl Acetals

1. General Procedure for the Preparation of Hydroxy-acetophenones

A suspension of the corresponding bromo-acetophenone (0.05 mmol) and sodium formate (17 g, 0.25 mol, 5 eq.) in aqueous ethanol (85%, 150 ml) was heated at reflux until completion of the reaction (TLC). Most of the ethanol was evaporated and the mixture partitioned between MTBE (80 ml) and water (70 ml). The organic phase was separated and washed with aqueous $NaHCO_3$ (sat.) and brine. Removal of the solvent in vacuo, after drying over $MgSO_4$, afforded a crude product as a solid which was recrystallised from ethanol.

2-Hydroxy-1-(4-methoxy-phenyl)-ethanone

Obtained according to the general procedure.

mp 104–105° C. $^1$H-NMR (400 MHz, $CDCl_3$): 3.48 (t, 1H, J 4); 4.82 (d, 2H, J 4); 6.95–7.0 (m, 2H); 7.85–7.95 (m, 2H). IR ($v_{max}$, $cm^{-1}$, neat): 3415m, 2929w, 1672s, 1603s. MS [m/z (EI)]: 166 ($M^+$, 4), 155 (100), 77 (28).

1-(3,5,5,6,8,8-Hexamethyl-5',6',7',8'-tetrahydro-naphthalen-2-yl)-2-hydroxy-ethanone Obtained according to the general procedure.

mp 81–82° C. $^1$H-NMR (400 MHz, $CDCl_3$): 1.0 (d, 3H, J 6.8); 1.08 (s, 3H); 1.26 (s, 3H); 1.31 (s, 3H); 1.33 (s, 3H); 1.41 (dd, 1H, J 13.2, 2.4); 1.63 (dd, 1H, J 13.2, 13.2); 1.8–1.95 (m, 1H); 2.54 (s, 3H); 4.76 (s, 2H); 7.26 (s, 1H);

7.57 (s, 1H). IR ($v_{max}$, cm$^{-1}$, neat): 3447w, 2963m, 2911m, 1675s, 1607w. MS [m/z (EI)]: 274 (M$^+$, 3), 243 (100).

2-Hydroxy-1-naphthalen-2-yl-ethanone

Obtained according to the general procedure.

mp 114–115° C. $^1$H-NMR (400 MHz, CDCl$_3$): 3.59 (t, 1H, J 4.4); 5.02 (d, 2H, J 4.4); 7.55–7.7 (m, 2H); 7.85–8.0 (m, 4H); 8.43 (s, 1H). IR ($v_{max}$, cm$^{-1}$, neat): 3428m, 3391m, 3051w, 2931w, 1680s, 1627m. MS [m/z (EI)]: 186 (M$^+$, 12), 155 (75), 127 (100), 40 (26), 28 (41).

2. General Procedure for the Preparation of Lactols

Lactols were obtained by reduction of the corresponding lactone: a suspension of the lactone (0.1 mol) in toluene (150 ml) was cooled –78° C. (CO$_2$/acetone) and treated with a solution of DIBAL-H (~1 M in hexanes, 110 ml, 0.11 mol, 1.1 equivalents). After the reaction was finished, methanol (85 ml) was slowly added and the reaction mixture allowed to warm to room temperature. Then a solution of potassium sodium tartrate (Rochelle's salt) (30% aq.) was added and the mixture stirred for 45 minutes, whereafter the phases separated well. The aqueous phase was extracted with MTBE, and the combined organic layers were washed twice with potassium sodium tartrate (Rochelle's salt) (30% aq.) and dried over MgSO$_4$. The crude obtained after removal of the solvents was purified by distillation under reduced pressure to afford a colorless oil.

8-Methyl-1-oxa-spiro[4.5]decan-2-ol

Obtained as a mixture of diastereomers (ratio 1:4) from Methyl LAITONE® according to the general procedure.

bp$_{0.06\ Torr}$: 72–73° C. $^1$H-NMR (400 MHz, CDCl$_3$): 0.8–1.05 (m, 2H); 0.88 (d, 3H, J 6.4); 1.2–1.55 (m, 4H); 1.6–1.75 (m, 2H); 1.8–2.1 (m, 5H); 3.67 (s, 0.2H); 3.83 (s, 0.8H); 5.50 (m, 1H). IR ($v_{max}$, neat, cm$^{-1}$): 3400mbr, 2925s, 2855m, 1774w. MS [m/z (EI)]: 170 (M$^+$, 1), 152 (47), 113 (39), 108(28), 96 (25), 95 (100), 93 (31), 81 (70), 79 (29), 70 (22), 67 (46), 55 (46), 53 (20), 41 (37), 39 (27).

5-Heptyl-tetrahydro-furan-2-ol

Obtained as a mixture of diastereomers (ratio 2:3) from PEACH PURE® according to the general procedure.

bp$_{0.07}$ Torr: 96–98° C. $^1$H-NMR (400 MHz, CDCl$_3$): 0.88 (t, 3H, J 6.8); 1.2–1.5 (m, 11H); 1.5–1.65 (m, 1H); 1.65–1.8 (m, 1H); 1.8–1.9 (m, 1H); 1.9–2.0 (m, 1H); 2.0–2.17 (m, 1H); 2.98 (d, 0.4H, J 2.4); 3.07 (d, 0.6H, J 2.4); 3.95–4.02 (m, 0.4H); 4.15–4.25 (m, 0.6H); 5.45–5.5 (m, 0.4H); 5.52–5.6 (m, 0.6H). IR ($v_{max}$, neat, cm$^{-1}$): 3405mbr, 2926s, 2856m, 1780w. MS [m/z (EI)]: 185 (M$^+$-H, 1), 87 (100), 69 (41), 55 (22) 43 (30), 41 (27).

6-(Pent-3-enyl)-tetrahydro-pyran-2-ol

Obtained as a mixture of diastereomers (ratio 35:65) from JASMOLACTONE® according to the general procedure, without final distillation.

$^1$H-NMR (400 MHz, CDCl$_3$): 1.1–1.25 (m, 0.35H); 1.25–1.4 (m, 0.65H); 1.4–1.75 (m, 7H); 1.75–1.9 (m, 2H); 2.0–2.2 (m, 2H); 2.3–2.37 (m, 0.65H); 2.42–2.5 (m, 0.35H); 2.9 (s, 0.35H); 3.37–3.45 (m, 0.65H); 3.52 (s, 0.65H); 3.9–4.0 (m, 0.35H); 4.69 (d, 0.65H, J 9.2); 5.3 (s, 0.35H); 5.35–5.5 (m, 2H). IR ($v_{max}$, neat, cm$^{-1}$): 3394mbr, 2936m, 2857m, 1719m. MS [m/z (EI)]: 170 (M$^+$, 1), 152 (M-H$_2$O, 23), 98 (36), 95 (21), 83 (22), 81 (48), 79 (25), 69 (23), 68 (26), 67 (40), 56 (24), 55 (100) 41 (41), 39 (26).

3. General Procedure for the Preparation of the Acetylated Lactols.

A cold (0° C.) solution of the lactol (50 mmol) in dichloromethane (75 ml) was treated with acetic anhydride (9.5 ml, 100 mmol, 2 eq.) and triethylamine (13.9 ml, 100 mmol, 2 eq.). After stirring overnight at room temperature, the mixture was poured into cold water and the separated aqueous phase was extracted with MTBE. The combined organic layers were washed with water and brine, and dried over MgSO$_4$. Removal of the solvents afforded a colorless oil which was used without further purification.

Acetic Acid 8-methyl-1-oxa-spiro[4.5]dec-2-yl ester

Obtained according to the general procedure.

$^1$H-NMR (400 MHz, CDCl$_3$): 0.9–1.05 (m, 2H); 0.89 (d, 3H, J 6.4); 1.3–1.45 (m, 2H); 1.45–1.6 (m, 2H); 1.7–1.95 (m, 5H); 2.0–2.2 (m, 2H); 2.02 (s, 3H); 6.24 (d, 1H, J 4.4). IR ($v_{max}$, neat, cm$^{-1}$): 2928m, 2857m, 1740s. MS [m/z (EI)]: 212 (M$^+$, 1), 152 (53), 108(28), 96 (24), 95 (100), 93 (31), 81 (70), 79 (28), 70 (22), 67 (41), 55 (34), 45 (23), 43 (36), 41 (31), 39 (24).

Acetic Acid 5-heptyl-tetrahydro-furan-2-yl Ester

Obtained as a mixture of diastereomers (ratio 45:55) according to the general procedure.

$^1$H-NMR (400 MHz, CDCl$_3$): 0.88 (t, 3H, J 6.6); 1.2–1.8 (m, 14H); 1.9–2.2 (m, 2H); 2.03 (s, 1.35H); 2.04 (s, 1.65H); 4.02–4.12 (m, 0.45H); 4.17–4.22 (m, 0.55H); 6.23 (m, 0.45H); 6.28 (m, 0.55H). IR ($v_{max}$, neat, cm$^{-1}$): 2927m, 2856m, 1780m, 1742s. MS [m/z (EI)]: 228 (M$^+$, 1), 168 (35), 84 (54), 83 (59), 82 (37), 81 (26), 71 (33), 70 (54), 69 (100), 68 (23), 67 (26), 57 (48), 56 (34), 55 (67), 43 (39), 41 (67), 39 (28), 29 (24).

Acetic Acid 6-pent-3-enyl-tetrahydro-pyran-2-yl Ester

Obtained as a mixture of diastereomers (ratio 1:1) according to the general procedure.

$^1$H-NMR (400 MHz, CDCl$_3$): 1.15–1.3 (m, 1H); 1.4–1.7 (m, 8H); 1.75–1.85 (m, 1H); 1.85–1.95 (m, 1H); 2.0–2.15 (m, 1H); 2.1 (s, 3H); 2.3–2.37 (m, 0.5H); 2.4–2.5 (m, 0.5H); 3.47–3.55 (m, 1H); 5.35–5.5 (m, 2H); 5.63 (m, 1H). IR ($v_{max}$, neat, cm$^{-1}$): 2940w, 1743m. MS [m/z (EI)]: 212 (M$^+$, 1), 95 (24), 81 (55), 79 (27), 68 (26), 67 (41), 57 (28), 55 (100), 53 (20), 45 (20), 43 (42), 41 (40), 39 (32), 29 (25).

4. General Procedure for the Preparation of the Cyclic Vinyl Ethers

Cyclic vinyl ethers were obtained by pyrolysis: a solution of the acetyl derivative (50 nmol) in toluene (100 ml) was dropped through a hot (260° C.) vertical PYREX® tube (32 cm in length, 2 cm in diameter) filled with PYREX® Raschig rings (5 mm in height, 3 mm in diameter) under normal pressure. The reaction solution was collected in a cold flask (CO$_2$/acetone) and washed with aq. NaHCO$_3$ (sat.) and brine. After drying over MgSO$_4$ and removal of the solvents, the crude was purified by distillation.

8-Methyl-1-oxa-spiro[4.5]dec-2-ene

Obtained according to the general procedure.

bp$_{0.1}$ Torr: 50° C. (Kugelrohr) $^1$H-NMR (400 MHz, CDCl$_3$): 0.90 (d, 3H, J 6.8); 0.95–1.1 (m, 2H); 1.25–1.65 (m, 5H); 1.65–1.85 (m, 4H); 4.75 (m, 1H); 6.25 (m, 1H) IR ($v_{max}$, neat, cm$^{-1}$): 2927s, 2855m, 1743m, 1621m. MS [m/z (EI)]: 152 (M$^+$, 54) 108 (30), 96 (26), 95 (100) 93 (33), 81 (76), 79 (30), 70 (23), 67 (44), 55 (35), 53 (20), 41 (31), 39 (26).

2-Heptyl-2,3-dihydro-furan bp$_{12\ mbar}$: 90–91° C. $^1$H-NMR (400 MHz, CDCl$_3$): 0.88 (t, 3H, J 8); 1.2–1.45 (m, 10H); 1.5–1.6 (m, 1H); 1.65–1.75 (m, 1H); 2.2–2.3 (m, 1H); 2.65–2.72 (m, 1H); 4.47–4.55 (m, 1H); 4.84 (m, 1H); 6.26 (m, 1H). IR ($v_{max}$, neat, cm$^{-1}$): 2926s, 2856m, 1731w, 1619m. MS [m/z (EI)]: 168 (M$^+$, 37), 84 (53), 83 (60), 82 (36), 81 (23), 71 (32), 70 (54), 69 (100), 68 (25), 67 (28), 57 (59), 56 (41), 55 (84), 54 (23), 43 (51), 42 (22), 41 (95), 39 (40), 29 (36), 27 (23).

2-Pent-3-enyl-3,4-dihydro-2H-pyran bp$_{0.1\ Torr}$: 50–60° C. (Kugelrohr) $^1$H-NMR (400 MHz, CDCl$_3$): 1.45–1.75 (m, 6H); 1.77–1.9 (m, 1H); 1.9–2.0 (m, 1H); 2.0–2.2 (m, 3H); 3.75–3.82 (m, 1H); 4.62–4.7 (m, 1H); 5.35–5.52 (m, 2H); 6.36 (d, 1H, J 8). IR ($v_{max}$, neat, cm$^{-1}$): 3060w, 2920m, 2851w, 1650m. MS [m/z (EI)]: 152 (M$^+$, 15), 95 (25), 81 (55), 79 (28), 68 (26), 67 (41), 57 (28), 55 (100), 53 (20), 41 (38), 39 (32), 29 (23).

5. Preparation of Cyclic Phenacyl Acetals (Fragrance Precursors)

Method A:

The cyclic vinyl ether (2 eq.) was added to a suspension of the hydroxy-acetophenone (10 mmol) in toluene (10 ml), followed by trifluoroacetic acid (2 or 3 drops, ~0.01 eq.). The mixture was heated at 50° C. When the reaction was complete (TLC, 2–3 hours), it was diluted with MTBE and poured into aq. NaHCO$_3$ (sat.). The aqueous phase was separated and extracted with MTBE, and the combined organic layers were washed with brine and dried over MgSO$_4$. The crude, obtained after evaporation of the solvents, was purified by chromatography (SiO$_2$, EtOAc/Hexane) to afford the desired product as a colorless to pale yellow oil.

Method B:

The acetyl derivative derived from the fragrant lactone (5 mmol) and pyridine (3–4 drops, 0.1 eq.) was added to a suspension of the hydroxy-acetophenone (10 mmol) in toluene (10 ml) The mixture was heated under reflux overnight. It was then poured into aq. NaHCO$_3$ (sat.) and the separated aqueous phase was extracted with MTBE. The combined organic layers were washed with brine and dried over MgSO$_4$. The crude, obtained after evaporation of the solvents, was purified by chromatography (SiO$_2$, EtOAc/Hexane) to afford the desired product as a colorless to pale yellow oil.

1-(3,5,5,6,8,8-Hexamethyl-5,6,7,8-tetrahydro-naphtalen-2-yl)-2-(8-methyl-1-oxa-spiro[4.5]dec-2-yloxy)-ethanone (1)

Obtained as a separable mixture of diastereomers (ratio 6:1) according to method A.

$^1$H-NMR (400 MHz, CDCl$_3$): major diastereomer: 0.88 (d, 3H, J 6.8); 0.95–1.02 (m, 2H); 0.99 (d, 3H, J 6.8); 1.06 (s, 3H); 1.25 (s, 3H); 1.30 (s, 3H); 1.32 (s, 3H); 1.35–1.8 (m, 9H); 1.8–1.95 (m, 3H); 2.0–2.1 (m, 1H); 2.13–2.22 (m, 1H); 2.48 (s, 3H); 4.72 (m, 2H); 5.21 (m, 1H); 7.20 (s, 1H); 7.54 (s, 1H). minor diastereomer: 0.9 (d, 3H, J 6.8); 0.9–1.02 (m, 2H); 0.99 (d, 3H, J 6.8); 1.07 (s, 3H); 1.27 (m, 3H); 1.32 (s, 3H); 1.33 (s, 3H); 1.25–1.8 (m, 9H); 1.82–2.0 (m, 3H); 2.0–2.2 (m, 2H); 2.54 (s, 3H); 4.67–4.8 (m, 2H); 5.38 (dd, 1H, J 4.8, 1.2); 7.21 (s, 1H); 7.56 (s, 1H). IR ($v_{max}$, neat, cm$^{-1}$): 2960m, 2925m, 1681m, 1607w, 1544w. UV [λ (ε), CH$_2$Cl$_2$, nm]: 217 (18273), 258 (10652). MS [m/z (EI)]: 426 (M$^+$, 1), 258 (20), 244 (25), 243 (100), 153 (96), 152 (38), 135 (84), 81 (24), 69 (24), 67 (25), 55 (22), 43 (22), 41 (25).

2-(5-Heptyl-tetrahydro-furan-2-yloxy)-1-(3,5,5,6,8,8-hexamethyl-5,6,7,8-tetrahydro-naphtalen-2-yl)-ethanone (2)

Obtained as a separable mixture of diastereomers (ratio 1:1) according to method A.

$^1$H-NMR (400 MHz, CDCl$_3$): 1$^{st}$ diastereomer: 0.87 (t, 3H, J 7.2); 0.99 (d, 3H, J 6.8); 1.06 (s, 3H); 1.26 (s, 3H); 1.31 (s, 3H); 1.32 (s, 3H); 1.2–1.5 (m, 12H); 1.55–1.7 (m, 2H); 1.8–1.95 (m, 2H); 2.0–2.15 (m, 3H); 2.48 (s, 3H); 3.9–4.0 (m, 1H); 4.65–4.75 (m, 2H); 5.25 (m, 1H); 7.2 (s, 1H); 7.56 (s, 1H). 2$^{nd}$ diastereomer: 0.87 (t, 3H, J 7.2); 0.99 (d, 3H, J 6.8); 1.06 (s, 3H); 1.26 (s, 3H); 1.31 (s, 3H); 1.32 (s, 3H); 1.2–1.5 (m, 12H); 1.55–1.7 (m, 2H); 1.8–2.05 (m, 4H); 2.48 (s, 3H); 4.0–4.1 (m, 1H); 4.65–4.8 (m, 2H); 5.2 (m, 1H); 7.21 (s, 1H); 7.55 (s, 1H). IR ($v_{max}$, neat, cm$^{-1}$): 2957m, 2926s, 2856m, 1684m, 1608w, 1545w. UV [λ (ε), CH$_2$Cl$_2$, nm]: 217 (14652), 258 (8060). MS [m/z (EI)]: 442 (M$^+$), 258 (19), 244 (30), 243 (100), 169 (27), 95 (39), 81 (20), 69 (27).

2-(5-Heptyl-tetrahydro-furan-2-yloxy)-1-naphtalen-2-yl-ethanone (3)

Obtained as a separable mixture of diastereomers (ratio 3:2) according to method A.

$^1$H-NMR (400 MHz, CDCl$_3$) major diastereomer: 0.87 (t, 3H, J 6.8); 1.2–1.35 (m, 10H); 1.35–1.5 (m, 2H); 1.5–1.6 (m, 1H); 2.05–2.17 (m, 3H); 3.87 (s, 3H); 3.95–4.05 (m, 1H); 4.91 (d, 1H, J 16.8); 5.01 (d, 1H, J 16.8); 5.30 (dd, 1H, J 4.6, 1.4); 7.52–7.65 (m, 2H); 7.85–8.05 (m, 4H); 8.47 (s, 1H). minor diastereomer: 0.85 (t, 3H, J 7); 1.2–1.5 (m, 10H); 1.55–1.7 (m, 2H); 1.7–1.82 (m, 1H); 1.95–2.05 (m, 2H); 2.17–2.25 (m, 1H); 4.0–4.1 (m, 1H); 4.90 (d, 1H, J 16.4); 5.03 (d, 1H, J 16.4); 5.25 (m, 1H); 7.52–7.65 (m, 2H); 7.85–8.05 (m, 4H); 8.47 (s, 1H). IR ($v_{max}$, neat, cm$^{-1}$): 2926s, 2855m, 1697s, 1628m, 1597w. UV [λ (ε), CH$_2$Cl$_2$, nm]: 250 (54627), 284 (10571). MS [m/z (EI)]: 354 (M$^+$, 1), 170 (57), 169 (46), 155 (31), 151 (21), 141 (22), 127 (36), 109 (29), 95 (100), 83 (25), 81 (46), 69 (31), 67 (35), 57 (24), 55 (33), 43 (30), 41 (33).

2-(5-Heptyl-tetrahydro-furan-2-yloxy)-1-(4-methoxyphenyl)-ethanone (4)

Obtained as a separable mixture of diastereomers (ratio 1:1) according to method B.

$^1$H-NMR (400 MHz, CDCl$_3$): 1$^{st}$ diastereomer: 0.88 (t, 3H, J 7); 1.2–1.35 (m, 10H); 1.35–1.47 (m, 2H); 1.5–1.57 (m, 1H); 2.0–2.15 (m, 3H); 3.87 (s, 3H); 3.95–4.02 (m, 1H); 4.73 (d, 1H, J 16.4); 4.83 (d, 1H, J 16.4); 5.25 (m, 1H); 6.91–6.95 (m, 2H); 7.91–7.95 (m, 2H). 2$^{nd}$ diastereomer: 0.88 (t, 3H, J 7); 1.2–1.5 (m, 11H); 1.57–1.65 (m, 1H); 1.7–1.8 (m, 1H); 1.9–2.02 (m, 2H); 2.15–2.22 (m, 1H); 3.87 (s, 3H); 4.0–4.1 (m, 1H); 4.72 (d, 1H, J 16); 4.84 (d, 1H, J 16); 5.19 (m, 1H); 6.91–6.95 (m, 2H); 7.91–7.95 (m, 2H). IR ($v_{max}$, neat, cm$^{-1}$): 2927m, 2855m, 1777w, 1693m, 1601s, 1576m. UV [λ (ε), CH$_2$Cl$_2$, nm]: 218 (5724), 272 (8235). MS [m/z (EI)]: 334 (M$^+$), 169 (31), 151 (26), 150 (78) 135 (71), 109 (24), 95 (100), 81 (37), 69 (22), 67 (22), 55 (20).

1-(3,5,5,6,8,8-Hexamethyl-5,6,7,8-tetrahydro-naphthalen-2-yl)-2-(6-pent-3-enyl-tetrahydro-pyran-2-yloxy)-ethanone (5)

Obtained as a mixture of diastereomers according to method A.

$^1$H-NMR (400 MHz, CDCl$_3$) major diastereomer: 0.99 (d, 3H, J 6.8); 1.07 (s, 3H); 1.26 (s, 3H); 1.31 (s, 3H); 1.33 (s, 3H); 1.37–1.7 (m, 11H); 1.8–2.2 (m, 5H); 2.19 (s, 3H); 3.7–3.8 (m, 1H); 4.73 (s, 2H); 4.97 (m, 1H); 5.34–5.5 (m, 2H); 7.22 (s, 1H); 7.57 (s, 1H). IR ($v_{max}$, neat, cm$^{-1}$): 2934s, 1698m, 1608w. UV [λ (ε), CH$_2$Cl$_2$, nm]: 213 (15336), 258 (8487) MS [m/z (EI)]: 426 (M$^+$, 1), 243 (100), 153 (18), 135 (43) 85 (33), 55(25).

1-(Naphtalen-2-yl)-2-(6-pent-3-enyl-tetrahydro-pyran-2-yloxy)-ethanone (6)

Obtained as a separable mixture of diastereomers (ratio 19:1) according to method A.

$^1$H-NMR (400 MHz, CDCl$_3$): major diastereomer: 1.4–1.75 (m, 9H); 1.9–2.2 (m, 4H); 3.75–3.82 (m, 1H); 4.9–5.05 (m, 3H); 5.35–5.5 (m, 2H); 7.55–7.65 (m, 2H); 7.85–8.05 (m, 4H); 8.47 (s, 1H). minor diastereomer: 1.4–1.75 (m, 9H); 1.9–2.2 (m, 4H); 3.3–3.4 (m, 1H); 5.0–5.2 (m, 3H); 5.35–5.5 (m, 2H); 7.55–7.65 (m, 2H); 7.85–8.05 (m, 4H); 8.49 (s, 1H). IR ($v_{max}$, neat, cm$^{-1}$): 2936m, 1697s, 1628m, 1596w. UV [λ (ε), CH$_2$Cl$_2$, nm]: 250 (45352), 285 (8887). MS [m/z (EI)]: 338 (M$^+$, 4), 186 (22), 170 (100), 155 (79), 153 (37), 141 (26), 135 (83), 127 (64), 109 (32), 107 (27), 96 (24), 93 (37), 85 (69), 81 (31), 79 (30), 69 (43), 67 (40), 57 (26), 55 (70), 41 (21).

Example 2

Photolysis of Cyclic Phenacyl Acetals (I) in Solutions

Photorelease assays were conducted on solutions (typical concentrations of precursors (I) were from 0.05% to 0.1% g/v) in organic solvents (preferably ethanol) or on cotton towels after deposition of the phenacyl acetals (I), as described below in the example 3.

The solutions were irradiated with a mercury lamp (150 W) in a borosilicate glass apparatus (PYREX®) so as to limit the irradiation window to mainly the UVA and UVB spectrum of sun light. The alcoholic solution was irradiated for one hour and samples taken every 15 min to analyze the extent of the photolysis.

Analysis

The presence of the aryl ketone (II) and lactone (III) after photolysis in solutions was determined by using GC retention times. Samples (0.2 μl) were injected (on column injection) without further dilution. Gas chromatography-flame ionization detection (GC-FID) was carried out with a Fisons-GC 8000series apparatus, using a J&W Scientific DB-5 capillary column (30 m, 0.32 mm id, 0.25 μm film, He carrier gas, 85 kPa). The results are summarized in table 1.

Precursors derived from ORANGER CRYSTALS® cleaved fairly slowly, those derived from FIXOLIDE® cleaved quickly and acetanisole precursors even more quickly. The estimated half lives under the stated conditions were calculated from the GC analysis (corresponding peak area).

$t_{1/2}$ (Acetanisole)=7–8 min $t_{1/2}$ (FIXOLIDE®)=6–7 min $t_{1/2}$ (ORANGER CRYSTALS®)=30–35 min

TABLE 1

Release of aryl ketones (II) and lactone (III) from cyclic phenacyl acetals (I) in solution upon irradiation with a mercury lamp.

| STRUCTURE (I) | Fragrance Target | | UV-test* |
|---|---|---|---|
| | aryl ketone (II) | lactone (III) | |
| 1 | FIXOLIDE ® | PEACH PURE ® | +++ |
| 2 | ORANGER CRYSTALS ® | PEACH PURE ® | + |
| 3 | acetanisole | PEACH PURE ® | +++ |

*0: no cleavage,

+: slow cleavage,

++: medium cleavage,

+++: fast cleavage

Example 3

Spray Tests 1 g of an approximately 0.2% cyclic phenacyl acetal (I) solution in ethanol was evenly sprayed on a Terry towel (white cotton towel, 25cm×25 cm, 45 g), corresponding to 45–75 μg/g cotton. The sprayed towels were allowed to dry in a dark and odorless place. When dry, the towels were irradiated for a few seconds up to a few minutes with a tanning lamp (Osram ULTRA-VITALUX®, 300 W; at a distance of 50 cm, the light has approximately six to seven times the effect of the natural sunlight at noon on a sea-side mid-summer day). The evaluation was done by a trained panel of perfumers before and after irradiation. Before irradiation, the towels were judged to be odorless. The results after irradiation are summarized in table 2.

TABLE 2

Release of aryl ketones and lactones from cyclic phenacyl acetals on fabric upon irradiation with a tanning lamp.

| | | Fragrance Target (perception)* | | Global appreciation* |
|---|---|---|---|---|
| | STRUCTURE | aryl ketone (II) | lactone (III) | |
| 1 | 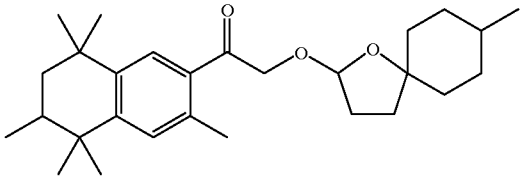 | FIXOLIDE ® (++) | METHYL LAITONE ® (+) | + |
| 2 | 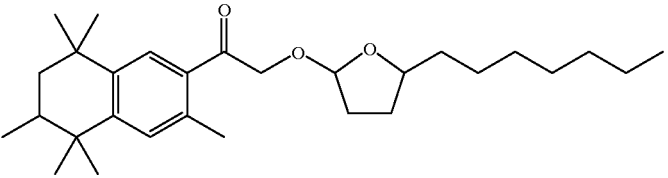 | FIXOLIDE ® (++) | PEACH PURE ® (++) | ++ |
| 3 | 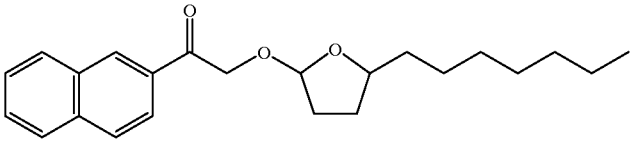 | ORANGER CRYSTALS ® (++) | PEACH PURE ® (++) | ++ |
| 4 | 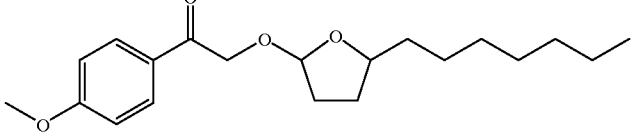 | Acetanisole (++) | PEACH PURE ® (++) | +++ |
| 5 | 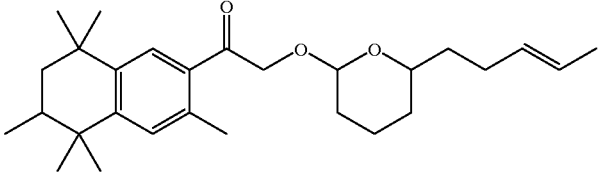 | FIXOLIDE ® (++) | JASMOLACTONE ® (+++) | +++ |

TABLE 2-continued

Release of aryl ketones and lactones from cyclic phenacyl acetals on fabric upon irradiation with a tanning lamp.

| STRUCTURE | Fragrance Target (perception)* | | Global appreciation* |
|---|---|---|---|
| | aryl ketone (II) | lactone (III) | |
| 6 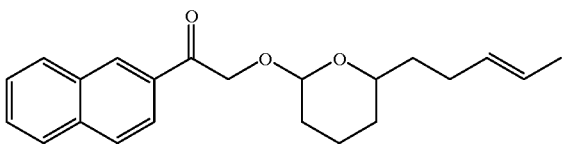 | ORANGER CRYSTALS ® (++) | JASMOLACTONE ® (++) | ++ |

*O: very weak,
+: weak,
++: medium,
+++: strong

Example 4

Stability Tests

The cyclic phenacyl acetals (I) were incubated in aqueous buffer solutions of pH 2.5, pH 7 and pH 9.5 for 24 h at 37° C. and were found to be stable in basic and neutral media, but less so under acidic conditions. The results are summarized in table 3.

TABLE 3

Stability of cyclic phenacyl acetals under different pH.

| STRUCTURE | pH 2.5 | pH 7 | pH 9.5 |
|---|---|---|---|
| 1 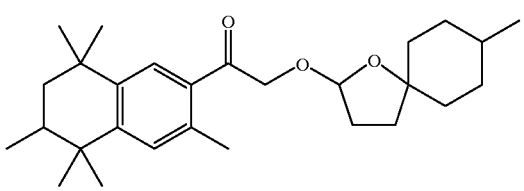 | stable | stable | stable |
| 2 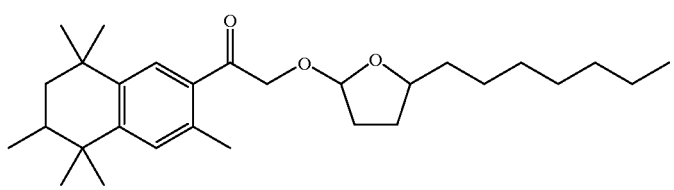 | stable | stable | stable |
| 3 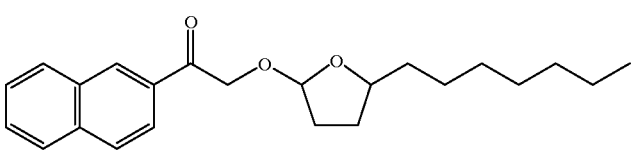 | unstable | stable | stable |

TABLE 3-continued

Stability of cyclic phenacyl acetals under different pH.

| STRUCTURE | pH 2.5 | pH 7 | pH 9.5 |
|---|---|---|---|
| 4 | unstable | stable | stable |
| 5 | stable | stable | stable |
| 6 | unstable | stable | stable |

The invention being thus described, it will be obvious that the same may be varied in many ways. Such variations are not to be regarded as a departure from the spirit and scope of the invention and all such modifications are intended to be included within the scope of the following claims.

What is claimed is:

1. A fragrance precursor of formula I:

(I)

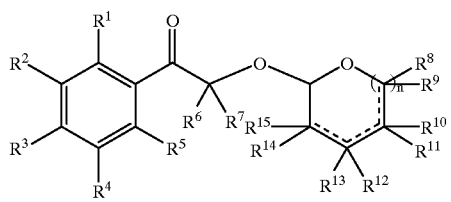

wherein the dotted lines indicating one or two optional double bonds in the cyclic acetal, that forms a fragrant ketone of formula II:

(II)

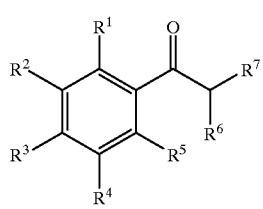

and a fragrant lactone of formula III:

(III)

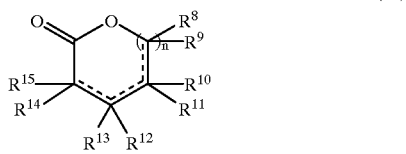

containing not more than 20 carbon atoms, wherein $R^1$ to $R^5$ represent independently H, —$NO_2$, linear or branched $C_1$–$C_6$-alkyl, $C_2$–$C_6$-alkenyl, $C_2$–$C_6$-alkynyl, or $C_1$–$C_4$-alkoxy, $R^1$ and $R^2$, $R^2$ and $R^3$, $R^3$ and $R^4$, and $R^4$ and $R^5$ may form together one or two aliphatic or aromatic rings, these rings may optionally contain linear or branched $C_1$–$C_4$-alkyl, $C_2$–$C_4$-alkenyl, or $C_2$–$C_4$-alkynyl residues, and these rings and residues may comprise one or more oxygen atoms, $R^6$ and $R^7$ are independently H, linear or branched $C_1$–$C_6$-alkyl-, $C_2$–$C_6$-alkenyl, or $C_2$–$C_6$-alkynyl, and $R^6$ or $R^7$ may form with either $R^1$ or $R^5$ a carbocyclic ring optionally substituted by an aliphatic residue, n is either 0 or 1, $R^8$ to $R^{15}$ are independently H, branched or linear $C_1$–$C_{15}$-alkyl, $C_2$–$C_{15}$-alkenyl, $C_2$–$C_{15}$-alkynyl, or $C_1$–$C_4$-alkoxy, they may form together one or more aliphatic or aromatic rings, these rings may optionally contain branched or linear $C_1$–$C_{10}$-alkyl, $C_2$–$C_{10}$-alkenyl, or $C_2$–$C_{10}$-alkynyl residues, and these rings and residues may comprise one or more oxygen atoms, or $R^8$ and $R^9$ together; $R^{10}$ and $R^{11}$ together; $R^{12}$ and $R^{13}$ together; or $R^{14}$ and $R^{15}$ together represent H, branched or linear $C_2$–$C_{15}$-alkyl, $C_2$–$C_{15}$-alkenyl, $C_2$–$C_{15}$- alkynyl or $C_1$–$C_4$-alkoxy when the ring carbon atom supporting these groups is unsaturated and with the proviso that fragrance precursors of formula (I) wherein
(1) the ring of the acetal is saturated, and n is 1, and all of $R^8$ to $R^{15}$ are H, or
(2) the ring of the acetal is saturated, and n is 1, and all of $R^{10}$ to $R^{15}$ are H and either $R^8$ is $C_6$ and $R^9$ is H or $R^9$ is $C_6$ and $R^8$ is H are excluded.

2. A fragrance precursor according to claim 1 wherein n is 0, one of the residues $R^{11}$ to $R^{15}$ is an aliphatic residue having 1 to 15 carbon atoms, and the other residues are H.

3. A fragrance precursor according to claim 1 wherein in formula I n is 0, $R^{10}$ is an aliphatic residue having 1 to 15 carbon atoms and $R^{11}$ to $R^{15}$ are H.

4. A fragrance precursor according to claim 1 wherein in formula I n is 0, two or more of the residues $R^{10}$ to $R^{15}$ are aliphatic residues having 1 to 15 carbon atoms, and the other residues are H.

5. A fragrance precursor according to claim 1 wherein in formula I n is 0, and $R^{10}$ and $R^{11}$ are aliphatic residues having 1 to 10 carbon atoms.

6. A fragrance precursor according to claim 1 wherein in formula I n is 0, and at least two of the residues $R^{10}$ to $R^{15}$ are residues having 1 to 15 carbon atoms and form together one or more carbocyclic ring(s), which may optionally be substituted with one or more aliphatic residue(s) having 1 to 10 carbon atoms.

7. A fragrance precursor according to claim 1 wherein in formula I n is 0, and $R^{10}$ and $R^{11}$ are residues having 1 to 15 carbon atoms and form together a ring which may be further substituted with one or more aliphatic residues having 1 to 10 carbon atoms.

8. A fragrance precursor according to claim 1 wherein in formula I n is 1, one or more of the residues $R^8$ to $R^{15}$ are an aliphatic residue having 1 to 15 carbon atoms, and the other residues are H.

9. A fragrance precursor according to claim 1 wherein in formula I n is 1, $R^8$ is an aliphatic residue having 1 to 15 carbon atoms, and $R^9$ to $R^{15}$ are H.

10. A fragrance precursor according to claim 1, wherein in formula I n is 1, at least two of the residues $R^8$ to $R^{15}$ are aliphatic and have 1 to 15 carbon atoms, and the other residues are H.

11. A fragrance precursor according to claim 1, wherein in formula I n is 1, and at least two of the residue $R^8$ to $R^{15}$ are residues having 1 to 15 carbon atoms and form together one or more carbocyclic ring(s), which may optionally be substituted with one or more aliphatic residues having 1 to 10 carbon atoms.

12. A fragrance precursor according to claim 1 wherein in formula I at least one of the residues $R^6$ and $R^7$ is H.

13. A fragrance precursor according to claim 1 wherein in formula I the residues $R^6$ and $R^7$ are H.

14. A fragrance precursor according to claim 1 wherein the residues $R^6$ and $R^7$ are H, and $R^1$ to $R^5$ represent independently H, —$NO_2$, linear or branched $C_1$–$C_6$-alkyl, $C_2$–$C_6$-alkenyl, $C_2$–$C_6$-alkynyl or $C_1$–$C_4$ alkoxy.

15. A fragrance precursor according to claim 1 wherein in formula I the fragrant ketone of formula II is selected from 1-phenyl-ethanone, 2,4-dimethylphenyl-ethanone, 1-[4-(1,1-dimethylethyl)-2,6-dimethylphenyl]-ethanone, 1-(4-tert-butyl-3,5-dinitro-2,6-dimethyl)-ethanone and 1-(4-methoxyphenyl)-ethanone.

16. A fragrance precursor according to claim 1 wherein in formula I $R^1$ and $R^2$, $R^2$ and $R^3$, $R^3$ and $R^4$, and $R^4$ and $R^5$, form together one or two aliphatic or aromatic rings which may optionally contain substituted or unsubstituted $C_1$–$C_4$-alkyl, $C_2$–$C_4$-alkenyl, $C_2$–$C_4$-alkynyl residues and may comprise one or more oxygen atoms.

17. A fragrance precursor according to claim 1 wherein the fragrant ketone of formula II is selected from the group consisting of 1-(2-naphtalenyl)-ethanone, 4-acetyl-6-tert-butyl-1,1-dimethyl-indan, 1-(5,6,7,8-tetrahydro-3',5',5',6',8',8'-hexamethyl-2-naphthalenyl)-ethanone, 1-(5,6,7,8-tetrahydro-3',5',5',8',8'-pentamethyl-2-naphthalenyl)-ethanone, 1-(5,6,7,8-tetrahydro-3'-ethyl-5',5',8',8'-tetramethyl-2-naphthalenyl)-ethanone, 1-(2,3-dihydro-1',1',2',3',3',6'-hexamethyl-1H-inden-5-yl-ethanone, 1-[2,3-dihydro-1',1',2',6'-tetramethyl-3-(1-methylethyl)-1H-inden-5-yl]-ethanone, 5-acetyl-1,1,2,3,3-pentamethyl-indane, 1-(5,6,7,8-tetrahydro-2-naphthalenyl)-ethanone.

18. A compound of formula I:

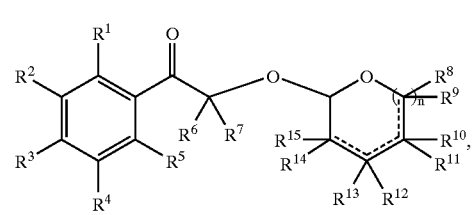

(I)

the dotted lines indicating one or two double bonds in the ring of the cyclic acetal, wherein $R^1$ to $R^5$ represent independently H, —$NO_2$, linear or branched $C_1$–$C_6$-alkyl, $C_2$–$C_6$-alkenyl, $C_2$–$C_6$-alkynyl, or $C_1$–$C_4$-alkoxy, $R^1$ and $R^2$, $R^2$ and $R^3$, $R^3$ and $R^4$, and $R^4$ and $R^5$ may form together one or two aliphatic or aromatic rings, these rings may optionally contain substituted or unsubstituted $C_1$–$C_4$-alkyl, $C_2$–$C_4$-alkenyl or $C_2$–$C_4$-alkynyl residues, and may comprise one or more oxygen atoms, $R^6$ and $R^7$ are independently H, linear or branched $C_1$–$C_6$-alkyl, $C_2$–$C_6$-alkenyl, $C_2$–$C_6$-alkynyl, and $R^6$ or $R^7$ may form with either $R^1$ or $R^5$ a substituted or unsubstituted carbocyclic ring, n is either 0 or 1, $R^8$ to are independently H, branched or linear $C_1$–$C_{15}$-alkyl, $C_2$–$C_{15}$-alkenyl, $C_2$–$C_{15}$-alkynyl or $C_1$–$C_4$-alkoxy, they may form together one ore more aliphatic or aromatic rings, these rings may optionally contain branched or linear $C_1$–$C_{10}$-alkyl, $C_2$–$C_{10}$-alkenyl or $C_2$–$C_{10}$-alkynyl residues, and the above rings and residues may comprise one or more oxygen atoms, and the cyclic acetal portion of the compound of formula (I), represented by formula Ib:

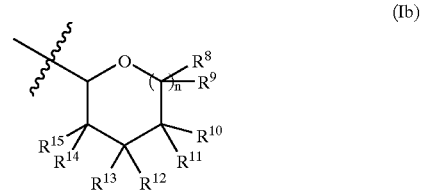

(Ib)

contains not more than 20 carbon atoms.

19. A compound of formula Ia:

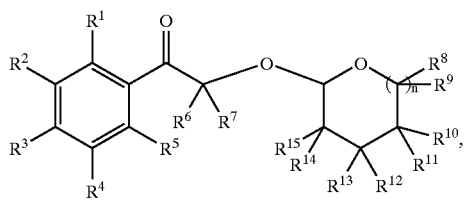

(Ia)

wherein the ring of the acetal is saturated, $R^1$ to $R^5$ represent independently H, —$NO_2$, linear or branched $C_1$–$C_6$-alkyl, $C_2$–$C_6$-alkenyl, $C_2$–$C_6$-alkynyl, or $C_1$–$C_4$-alkoxy, $R^1$ and $R^2$, $R^2$ and $R^3$, $R^3$ and $R^4$, and $R^4$ and $R^5$ may form together one or two aliphatic or aromatic rings, these rings may optionally contain substituted or unsubstituted $C_1$–$C_4$-alkyl, $C_2$–$C_4$-alkenyl or $C_2$–$C_4$-alkynyl residues, and may comprise one or more oxygen atoms, $R^6$ and $R^7$ are independently H, linear or branched $C_1$–$C_6$-alkyl, $C_2$–$C_6$-alkenyl, $C_2$–$C_6$-alkynyl, and $R^6$ or $R^7$ may form with either $R^1$ or $R^5$ a substituted or unsubstituted carbocyclic ring, n is 0, $R^8$ to $R^{15}$ are independently H, branched or linear $C_1$–$C_{15}$-alkyl, $C_2$–$C_{15}$-alkenyl, $C_2$–$C_{15}$-alkynyl or $C_1$–$C_4$-alkoxy, they may form together one aliphatic or aromatic ring, and the ring may optionally contain branched or linear $C_1$–$C_{10}$-alkyl, $C_2$–$C_{10}$-alkenyl or $C_2$–$C_{10}$-alkynyl residues, and the above rings and residues may comprise one or more oxygen atoms, and the cyclic acetal portion of the compound of formula (I), represented by formula Ib:

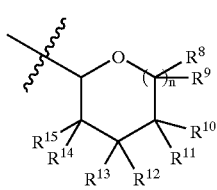

(Ib)

contains not more than 20 carbon atoms.

20. A compound of formula Ia:

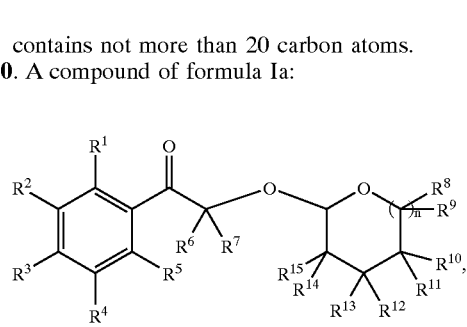

(Ia)

wherein the ring of the acetal is saturated, $R^1$ to $R^5$ represent independently H, —$NO_2$, linear or branched $C_1$–$C_6$-alkyl, $C_2$–$C_6$-alkenyl, $C_2$–$C_6$-alkynyl, or $C_1$–$C_4$-alkoxy, $R^1$ and $R^2$, $R^2$ and $R^3$, $R^3$ and $R^4$, and $R^4$ and $R^5$ may form together one or two aliphatic or aromatic rings, these rings may optionally contain substituted or unsubstituted $C_1$–$C_4$-alkyl, $C_2$–$C_4$-alkenyl or $C_2$–$C_4$-alkynyl residues, and may comprise one or more oxygen atoms, $R^6$ and $R^7$ are independently H, linear or branched $C_1$–$C_6$-alkyl, $C_2$–$C_6$-alkenyl, $C_2$–$C_6$-alkynyl, and $R^6$ or $R^7$ may form with either $R^1$ or $R^5$ a substituted or unsubstituted carbocyclic ring, n is 1, $R^8$ to $R^{15}$ are independently H, branched or linear $C_1$–$C_{15}$-alkyl, $C_2$–$C_{15}$-alkynyl or $C_1$–$C_4$-alkoxy, they may form together one or more aliphatic or aromatic rings, these rings may optionally contain branched or linear $C_1$–$C_{10}$-alkyl, $C_2$–$C_{10}$-alkenyl or $C_2$–$C_{10}$-alkynyl residues, and the above rings and residues may comprise one or more oxygen atoms, with the proviso that compounds wherein all of $R^8$ to $R^{15}$ are H, or all of $R^{10}$ to $R^{15}$ are H and either $R^8$ is $C_6$ and $R^9$ is H or $R^9$ is $C_6$ and $R^8$ is H are excluded, and the cyclic acetal portion of the compound of formula (I), represented by formula Ib:

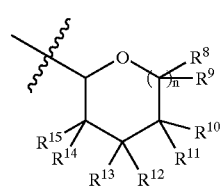

(Ib)

contains not more than 20 carbon atoms.

21. A perfumed product comprising the fragrance precursor of claim 1.

22. A perfumed product according to claim 21 wherein the perfumed product is selected from the group consisting of laundry compositions, cleaning products, body care products, and personal care products.

23. A process for providing a fragrance to a substrate comprising:

(a) treating a substrate with the perfumed product of claim 21; and (b) allowing the compound of formula I to be cleaved to form a fragrant ketone of formula II:

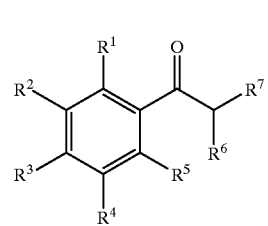

(II)

and a fragrant lactone of formula III:

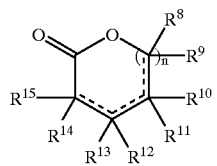

containing not more than 20 carbon atoms.

24. A process according to claim 23 wherein the compound of formula I is cleaved by exposure to light.

25. A process for providing a perfumed product comprising:
(a) forming a mixture by combining a base material with a fragrance precursor of claim 1; and
(b) forming a perfumed product from the mixture.

26. A process according to claim 25 wherein the perfumed product is selected from the group consisting of laundry compositions, cleaning products, body care products, and personal care products.

* * * * *